United States Patent
Hauser et al.

(10) Patent No.: US 11,485,945 B2
(45) Date of Patent: Nov. 1, 2022

(54) AUTONOMOUS MICROFLUIDIC DEVICE FOR SAMPLE PREPARATION

(71) Applicant: Intelligent Virus Imaging Inc., Southern Pines, NC (US)

(72) Inventors: Janosch Hauser, Älvsjö (SE); Gustaf Kylberg, Sollentuna (SE); Göran Stemme, Lidingö (SE); Ida-Maria Sintorn, Sollentuna (SE); Niclas Roxhed, Bromma (SE)

(73) Assignee: Intelligent Virus Imaging Inc, Southern Pines, NC (US)

( * ) Notice: Subject to any disclaimer, the term of this patent is extended or adjusted under 35 U.S.C. 154(b) by 249 days.

(21) Appl. No.: 17/025,390

(22) Filed: Sep. 18, 2020

(65) Prior Publication Data
US 2022/0081662 A1 Mar. 17, 2022

Related U.S. Application Data

(63) Continuation-in-part of application No. 17/023,922, filed on Sep. 17, 2020.

(51) Int. Cl.
*C12M 3/06* (2006.01)
*B01L 3/00* (2006.01)

(52) U.S. Cl.
CPC ........ *C12M 23/16* (2013.01); *B01L 3/502738* (2013.01); *B01L 2300/0864* (2013.01); *B01L 2400/0688* (2013.01)

(58) Field of Classification Search
CPC ........... B01L 3/502738; B01L 3/50273; B01L 2400/0406; B01L 2400/0688; B01L 3/5023; B01L 2200/0621; B01L 2200/0678; B01L 2300/069; B01L 2300/0816; B01L 2300/0874; B01L 2300/0887; B01L 2300/126; B01L 2400/0677; G01N 23/20025; G01N 1/30
See application file for complete search history.

(56) References Cited

PUBLICATIONS

Kinahan, David J., et al. "Laboratory unit operations on centrifugal lab-on-a-disc cartridges using dissolvable-film enabled flow control." (2014). (Year: 2014).*

* cited by examiner

*Primary Examiner* — Jennifer Wecker
*Assistant Examiner* — Oyeleye Alexander Alabi
(74) *Attorney, Agent, or Firm* — Fasth Law Offices; Rolf Fasth

(57) ABSTRACT

The method is for preparing a sample in a microfluidic device. A microfluidic device is provided that has a first reservoir in fluid communication with a second reservoir in fluid communication with and adjacent to a draining unit that has a first absorbing member disposed therein. The first reservoir contains a first liquid that is held in the first reservoir by a capillary stop valve connecting the first and second reservoirs. The second reservoir has a sample support disposed therein. A second liquid, containing substances, is added to the second reservoir. The second liquid contacts the first liquid and the first absorbing member. The first absorbing member absorbs the second liquid and the first liquid. The substances adhere to the sample support.

20 Claims, 22 Drawing Sheets

Sample addition

Sample adsorption

Liquid blotting

Empty inlet

|  | Manual count | True positives | False positives |
|---|---|---|---|
| # Particles | 605 | 557 | 29 |
| Ratio | — | 92.1% | 4.9% |

AUTONOMOUS MICROFLUIDIC DEVICE FOR SAMPLE PREPARATION

PRIOR APPLICATION

This is a continuation-in-part (CIP) patent application that claims priority from U.S. patent application Ser. No. 17/023,922, filed 17 Sep. 2020.

TECHNICAL FIELD

The present invention generally relates to a device and method for consistent and user-independent preparation of particulate or elongate fiber-like samples, such as microparticles, nanoparticles and/or micro/nano-sized fibers, for subsequent analysis using microscopy or other inspection techniques. In particular this is useful for applications in transmission electron microscopy (TEM) or scanning electron microscopy (SEM).

BACKGROUND AND SUMMARY OF THE INVENTION

A consistent, user-independent and repeatable sample preparation method is necessary for objective analysis of liquid samples of micro and nano-sized particles such as virus particles, virus-like particles, proteins, protein complexes, fibers, delivery vesicles, pharmaceuticals and inorganic particles.

For example, modified virus vectors are commonly used in gene therapy applications. Determining the ratio of infectious to un-infectious particles and debris/other material in the sample provides invaluable information about the quality and efficacy of the final gene therapy product and the upstream development processes.

SEM (Scanning Electron Microscopy) and nsTEM (Negative Stain Transmission Electron Microscopy) application are clinical diagnostic devices where SEM and nsTEM are used to detect and analyze infectious agents, such as viruses, for diagnostic purposes. Additionally, SEM and nsTEM are widely used in the characterization of biological and inorganic particles and materials in research, development, quality control of vaccines, pharmaceuticals and materials. The main advantage of SEM/nsTEM over chemical and bio-chemical characterization techniques is the possibility of directly visualizing the sample of interest. This makes it possible to determine, for example, the cell morphology or to identify the virus family of a pathogenic organism. In nsTEM, the image contrast is achieved through a heavy metal stain solution (uranyl acetate, phosphotungstic acid, etc.) that embeds and preserves the particles of interest.

The value of TEM as a first screening tool to identify viral pathogens in infectious diseases was demonstrated during the SARS epidemic 2003 where diagnostic TEM first indicated that the causative virus was a member of the coronavirus family. Considering the ability of emerging infectious agents, such as Ebola, Zika or SARS-COV2, to spread rapidly on an intercontinental level as a result of globalized trade and travel, and the risks of bioterrorist attacks due to the instability of the global political scene, it is clear that access to efficient TEM analysis is a vital part of our emergency preparedness, management and civil defence. This is in addition to TEM's routine clinical use and its use in process design and quality control in pharmaceutical development and production.

When imaged using TEM, the stain scatters more electrons than the particles in the sample. This results in an image where the particles appear bright on a dark background with a resolution in the order of a few nanometers. Conventionally, TEM grids are prepared by following a manual preparation protocol. This involves pipetting 3-5 µl of the sample liquid onto a TEM grid and then letting it adsorb for about 10-60 seconds depending on the specimen. Excess sample is then manually blotted off the grid by using blotting paper. Immediately after blotting the sample, 3-5 µl of an aqueous stain solution is added to the grid.

Excess stain is then blotted off ideally leaving a uniform thin layer or thin film of stain liquid covering the adsorbed specimen. This thin film is left to dry. The film embeds the specimen for TEM imaging and protects it from dehydration. The stain also increases the contrast. One problem is that this manual procedure is highly dependent on the skill of the operator which affects the preparation consistency and leads to unreliable results. Inconsistent timing of the manual steps and the final blotting are often the cause for bad TEM grid preparations.

Alternative methods for trying to obtain a consistent nsTEM sample preparation employ contact pin-printing techniques where pipetting robots automatically dispense liquids onto the TEM grid. These approaches have some advantages over the manual preparation such as reduction of liquid volumes and the possibility for automation. However, they require special instrumentation and are significantly more complex and time-consuming than the manual preparation protocol.

Also, a microfluidic device for nsTEM grid preparation has been described. The TEM grid is confined in a microfluidic channel and the liquid handling for the sample preparation is controlled by an external pressure pump. While this improves the preparation consistency over manual preparations, the approach requires significantly more liquid volume than the manual procedure. It also requires special equipment and involves the user to control the timing of every preparation step which makes the preparation method unreliable and inconsistent.

There are several hurdles that must be overcome to reach the feasibility of using electron microscopy in time and resource limited situations such as the development and quality control in the production of pharmaceuticals, material synthesis and routine clinical diagnostics. As indicated above, the expert task of preparing the sample for analysis is associated with extreme complexity. This makes the use of the TEM technology a craftsmanship limited to a small number of experts. A sample preparation method can be learnt in a month for a person that has basic laboratory skills but to master it takes about 10 years while still generating a significant expert variability. This means that even experts in the field cannot produce consistent results without undesirable variability.

Sample preparation is normally performed according to a standardized procedure. First the sample is supplied onto a sample support (which in the case of TEM is a metal grid that is about 3 mm in diameter) and left to adhere to the sample support. In the next step, excess sample solution is removed, and a stain to protect the particles and/or increase the contrast is instantly added. In the case of negative stain TEM, this stain is a heavy metal salt solution. Excess stain is then removed. The removal of excessive fluid/stain is done by blotting with a filter paper. An additional washing step subsequent to the removal of excessive fluid is sometimes done after the sample addition and prior to adding the stain. Alternatively, the addition of liquids can be done by dipping the grid into droplets of the liquids. These steps are typically carried out manually by the instrument operator and hence the results strongly depend on the operator's ability to consistently perform the correct procedure.

Also, regardless of how consistent and skilled the operator is, it is not possible to consistently control the forces the different preparation steps induce on the particles. This affects the quality of the prepared sample and limits the reliability of subsequent analysis results.

As indicated above, some automatic or semi-automated preparation methods have been suggested in the past. They rely on robotic dispensers, microfluidics using special equipment or special sample holders connected to a pipetting device. The robotic dispensers require only minute sample volume but instead rely on highly specialized equipment. The microfluidic-based sample preparation approach results in more consistent preparations but again rely on special equipment (special grid holder and external pressure pump) and require about 10-times larger sample volumes compared to manual preparation. A method using a special pipette tip with a pocket/slit holding the grid has also been suggested. This mprep-based approach also requires larger sample volumes and involves manual timing steps. In addition, the liquids are flushed on both sides of the grid that increase the risk for poor quality preparations.

Hence, there is a need for a more reliable and consistent nsTEM sample preparation method. The present invention provides a solution to the above described problems without having the user-bias and consistency problems associated with manual preparation, and without the drawbacks of quality, large sample volumes, expensive and special equipment associated with conventional automated approaches.

More particularly, the device and method of the present invention provides a consistent objective (user-independent) and reproducible preparation of samples of sub-visible particles for subsequent imaging and analysis. The method of the present invention is based on microfluidic technology combined with dissolvable films that act as delay valves and absorption membranes. It is all built into a disposable sample preparation device or card, and hence does not require any special equipment or large sample volumes. The different liquids flow over the grid in a sequential fashion with a certain delay and speed that is defined by the dissolvable films and design of the absorption membranes (filters).

This combination allows for a highly automated procedure where different sample preparation liquids are automatically flushed over the sample grid in a controlled and well-defined manner. Once the user has added the sample liquid, the entire grid preparation process is self-driven, self-contained or automatic because the various liquids are automatically driven through the device of the present invention, without requiring any additional input, by relying on capillary forces and other surface tension effects. It should be understood that the use of stain and sample liquids are merely illustrative examples of suitable liquids to be used in the device of the present invention. A wide variety of other liquids may be used, as required. The user interaction is reduced to just adding the sample liquid after pre-loading the stain to specific positions of the device in a non-time sensitive manner. The addition of the sample triggers a sequence of flushing steps over the sample grid with liquids (such as stains) which are either pre-added or pre-stored in the card/device. When the automatic preparation is completed, the operator then simply transfers the correctly prepared sample grid into the TEM or SEM microscope or even transfers the card itself into the SEM or light microscope.

The device of the present invention preferably constitutes or is realized as a disposable paper-based kit, consisting of containers for adding liquids and absorption membranes and where the grid onto which the sample is loaded is either pre-fitted or added by the user. In case of a pre-fitted grid, the user-input consists of only pipetting the stain (unless the stain is pre-loaded) and then the sample liquid into different containers in the device. The addition of the last liquid triggers the start of the autonomous preparation process where microfluidic forces drives the flow of the two liquids (i.e. the stain and the sample liquid) over the grid and where dissolvable valves control the timing of the process. The grid may be coated or covered with a thin carbon layer onto which the particles in the sample liquid are permitted to adsorb or adhere until the dissolvable membrane in the draining or unit is dissolved, so that the particles remain on the grid and are subsequently embedded by the stain liquid, as explained in detail below.

More particularly, the autonomous microfluidic device of the present invention is, preferably, for microscopy sample preparation. It should be understood that the use of laminates in the device is merely an illustrative example and the device of the present invention is not limited to using laminates. Any other fabrication method could be used such as molding.

The microfluidic device of the present invention has a first reservoir that preferably includes a first liquid or into which a first liquid is added. The first liquid is being held by a capillary stop valve in the first reservoir. A second reservoir is in fluid communication with the first reservoir. The second reservoir has a second liquid and a sample support disposed therein. The second reservoir has an inlet opening defined therein. A draining unit is adjacent to the second reservoir. The draining unit is being in fluid communication with the second reservoir. The draining unit has a first absorption member disposed therein.

In an alternative embodiment of the present invention, the microfluidic device has a channel defined therein and the first reservoir is in fluid communication with the second reservoir via the channel.

In yet an alternative embodiment of the present invention, the channel extends to an edge at the second reservoir.

In another alternative embodiment of the present invention, the sample support has a first width and the opening has a width that is substantially similar to the first width.

In an alternative embodiment of the present invention, the draining or blotting unit has a dissolvable membrane disposed therein below the first absorption member.

In another embodiment of the present invention, the draining unit has a second absorption member located below the dissolvable membrane so that the dissolvable membrane is disposed between the first absorbing member and the second absorbing member.

In yet another embodiment of the present invention, the first reservoir is a preloaded stain reservoir containing a stain liquid.

In an alternative embodiment of the present invention, the first liquid in the capillary stop valve extends between the edge and another surface edge of the channel.

In another embodiment of the present invention, the first absorption member is a first filter or paper and the second absorption member is a second filter or paper.

In yet another embodiment of the present invention, the dissolvable membrane is a film based on poly-vinyl-alcohol (PVA).

In another embodiment of the present invention, the sample support is a grid for negative-stain transmission electron microscopy preparation.

In an alternative embodiment of the device of the present invention, the first liquid is a stain.

In yet another embodiment, the device has an additional reservoir upstream of the first reservoir.

In another embodiment of the device of the present invention, the draining unit has a second dissolvable member below the second absorption member, and a third absorption member below the second dissolvable member.

In an alternative embodiment, the draining unit has a vent opening defined therein.

In yet an alternative embodiment, the draining unit has a second dissolvable member and a third absorption member disposed below the first dissolvable member.

The method of the present invention is for preparing a sample in a microfluidic device. A microfluidic device is provided having a first reservoir in fluid communication with a second reservoir in fluid communication with and adjacent to a draining unit having a first absorbing member disposed therein. The first reservoir contains a first liquid that is being held in the first reservoir by a capillary stop valve connecting the first and the second reservoirs. The second reservoir has a sample support disposed therein. A second liquid, containing substances, is added to the second reservoir. The second liquid contacts the first liquid and the first absorbing member. The first absorbing member absorbs the second liquid and the first liquid. The substances adhering to the sample support.

In an alternative method, the draining unit is provided with a dissolvable membrane upstream of the first absorbing member. The second liquid or the first liquid dissolving the dissolvable membrane prior to the first absorbing member absorbing the first and second liquids.

In another method, the substances adhere to the sample support while the second liquid or the first liquid dissolves the dissolvable membrane.

In yet another method, the capillary stop valve holding the first liquid in the first reservoir preventing the first liquid from flowing into the second reservoir prior to adding the second liquid to the second reservoir.

In another method, a portion of the first liquid embedding the substances adhered to the sample support.

In yet another method, the capillary stop valve is provided with an edge that separates the first reservoir from the second reservoir and the edge holding the first liquid in the first reservoir.

In another method, the dissolvable membrane is provided downstream of the first absorption member and a second absorption member downstream of the dissolvable membrane and the first absorption member absorbing the second liquid and permitting the second liquid to come into contact with the dissolvable member.

In yet another method, the second absorption member absorbing the second liquid and the first liquid after the dissolvable membrane has been dissolved.

In another method, the second liquid breaking a surface tension of the first liquid upon contact with the first liquid held in the capillary stop valve.

In yet another method, a time period required to dissolve the dissolvable membrane controlling a permitted time period for the substances to adhere to the sample support.

In another method, the second liquid contacting the absorbing member before the first liquid.

In yet another method, the first portion of the first liquid drying on the sample support.

In an alternative method, a portion of the first liquid forming a liquid film on the sample support, wherein the liquid film has a film thickness of less than 1 mm but more than 10 nm.

In yet another method, the sample support is dried within three minutes at an ambient temperature and 50% relative humidity.

In another method, the first liquid has a volume of between 0.1-50 µl.

In yet another method, the second liquid has a volume of between 0.1-50 µl.

In an alternative method of the present invention, the method is for preparing a sample in a microfluidic device. A microfluidic device is provided having a first reservoir in fluid communication with a second reservoir in fluid communication with and adjacent to a draining unit having a first absorbing member disposed therein. The first reservoir containing a first liquid. The first liquid being held in the first reservoir by a capillary stop valve connecting the first and second reservoirs. A user of the microfluidic device adding a sample support into the second reservoir. The user adding a second liquid, containing substances, to the second reservoir. The user waiting a waiting period of at least 20 seconds before removing the sample support from the second reservoir. During the waiting period, the second liquid contacting the first liquid and the first absorbing member. During the waiting period, the first absorbing member absorbing the second liquid and the first liquid. During the waiting period, the substances adhering to the sample support. At the end of the waiting period, the user removing the sample support from the second reservoir.

In another method, the draining unit is provided with a dissolvable membrane upstream of the first absorbing member and the second liquid dissolving the dissolvable member during the waiting period.

In yet another method, the first liquid forming a film on the sample support and embedding substances adhered to sample support.

In another method, the film drying on the sample support.

BRIEF DESCRIPTION OF THE DRAWINGS

The present invention is now described, by way of example, with reference to the accompanying drawings, in which.

DETAILED DESCRIPTION

A capillary-driven microfluidic device of the present invention is presented herein for sample preparation that requires the same small liquid volumes as the conventional manual procedure does, and which requires minimal user-interaction. More particularly, the sample support is preferably a grid, such as a TEM grid. The user merely initiates the autonomous sample preparation process, waits for about one minute and then extracts the TEM grid that is ready for imaging in a TEM or SEM microscope. The autonomous process of the present invention typically requires a film, that is soluble by the sample liquid, such as a PVA (polyvinyl alcohol) film for a water-based sample liquid, that automatically controls the time for sample adsorption and draining of excess liquids. Microfluidic consistency for five microfluidic devices is demonstrated below by comparing the timing and duration of the microfluidic TEM grid preparation events. Furthermore, the adjustability of the time-delay is explained for 15 devices using three different thicknesses of the water-soluble film (12 µm, 24 µm, 36 µm). Sample preparation consistency is examined by imaging five autonomously prepared TEM grids, with AAV (Adeno-associated virus) particles as sample and Methylamine Vanadate as stain.

A particle detection script, extracting morphological information such as the average particle size, was run on 45 microscopy images per grid to investigate whether the images are suitable for automated image analysis. The device of the present invention may also be used to prepare protein samples and fibers for TEM investigations and other stains may be used.

The device of the present invention adapts the sample preparation steps of the manual procedure and replaces user-interactions with automated and capillary-driven microfluidic events. The device is preferably, but not necessarily, designed for single-use and does not require special instrumentation.

Figure 1A:
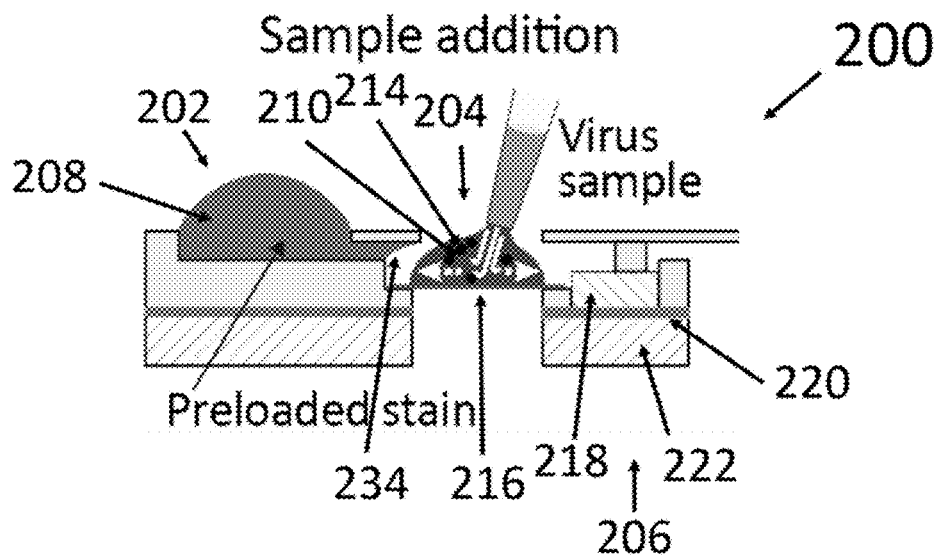
FIG. 1A is an elevational cross-sectional side view of the device of the present invention showing sample addition.

FIG. 1A-1D illustrate the conceptual sequence of the autonomous TEM grid preparation events in the device of the present invention. FIG. 1A shows how the step of adding the sample triggers the autonomous preparation process.

More particularly, the device 200 has a stain reservoir 202 adjacent to a sample reservoir or grid chamber 204. The sample reservoir is adjacent to a draining or blotting unit 206. The stain reservoir 202 holds or contains a stain liquid 208. Preferably, the stain liquid 208 is preloaded prior to use. The sample reservoir 204 contains a sample liquid 210 that includes substances 214, such as objects, molecules or particles, to be analyzed. The particles could be virus or virus-like particles or any other type of fibrous or particulate biological or inorganic object.

Figure 1B:
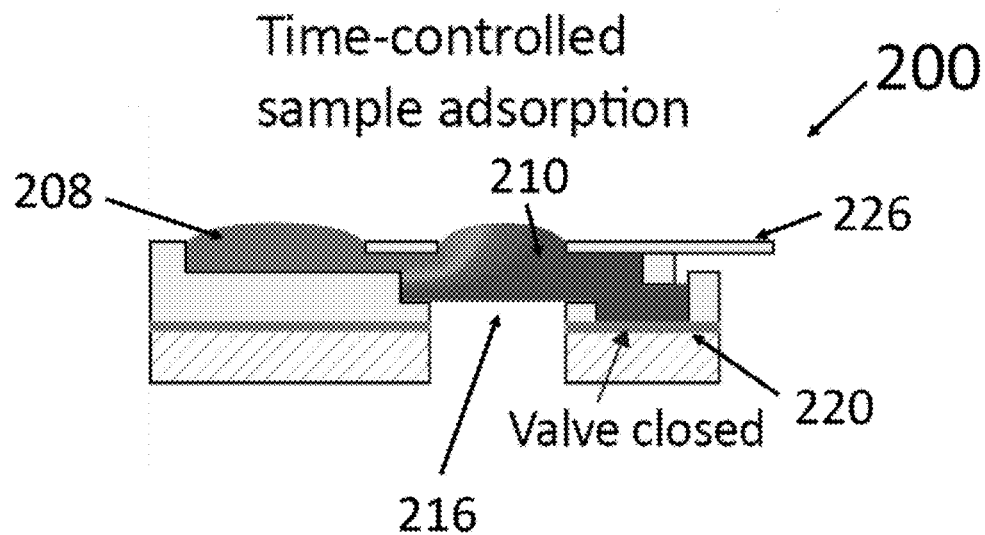
FIG. 1B is an elevational cross-sectional side view of the device of the present invention showing time-controlled sample adsorption.

When the sample liquid 210 is applied into the sample reservoir 204, the liquid 210 covers a sample support 216 such as a TEM grid and connects to the preloaded stain 208 upstream of the sample support or grid 216 and to a blotting paper or filter 218 in the draining or blotting unit 206 that is located downstream of the grid 216. The contact between the sample liquid 210 and the absorption units in the draining unit 206 starts the time-controlled sample adsorption step (as shown in FIG. 1B). When the sample liquid 210 is deposited or added into the sample reservoir 204, the sample liquid 210 comes into contact with a first absorption unit 218 (such as a first blotting/filter paper) of the draining unit 206. The draining unit 206 has a dissolvable valve or membrane 220 located below the first absorption unit 218. The sample liquid 210 covers the TEM grid 216 while the dissolvable valve 220, that separates the first blotting paper 218 from a second absorption unit such as a second blotting/filter paper 222, is closed. The valve 220 is closed until it has been dissolved by the liquid absorbed by the first absorption member 218. The time it takes to dissolve the dissolvable valve or membrane 220 is a critical step of the present invention because during this time, the particles 214 in the sample liquid 210 are permitted to adhere to or be adsorbed by the grid 216.

Figure 1C:
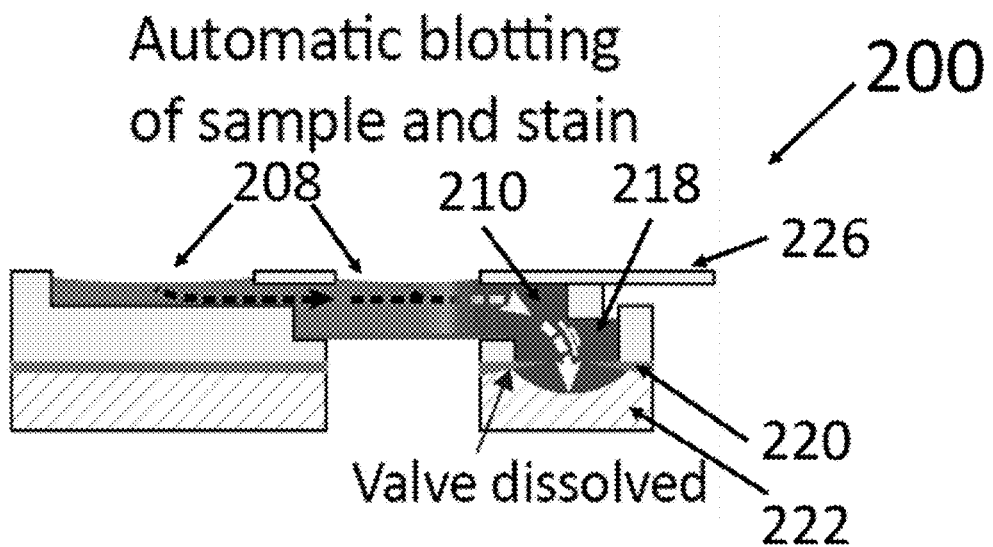
FIG. 1C is an elevational cross-sectional side view of the device of the present invention showing automatic draining of excessive sample and stain.
Figure 1D:
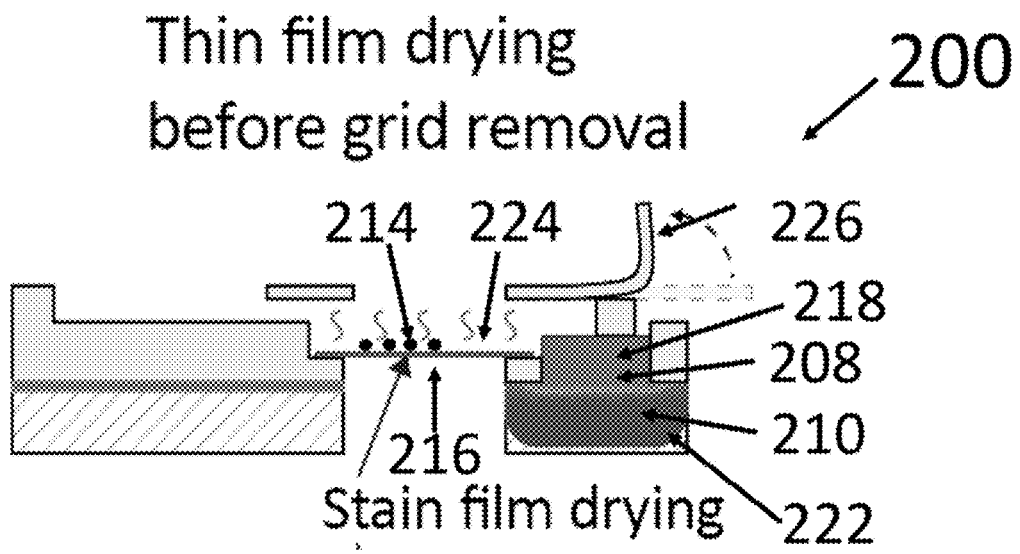
FIG. 1D is an elevational cross-sectional side view of the device of the present invention showing film drying before grid removal.
Figure 2A:
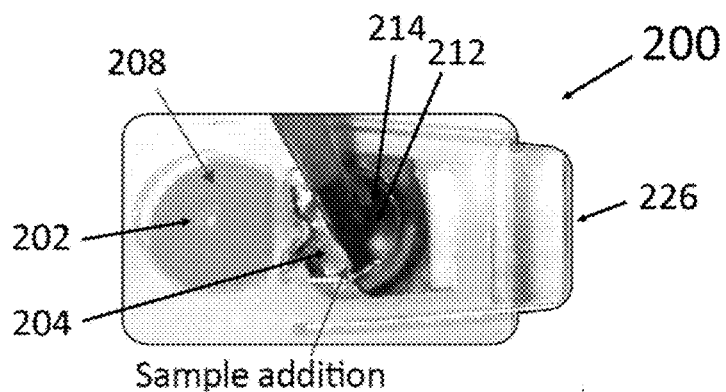
FIG. 2A is a top view of the device shown in FIG. 1A.
Figure 2B:
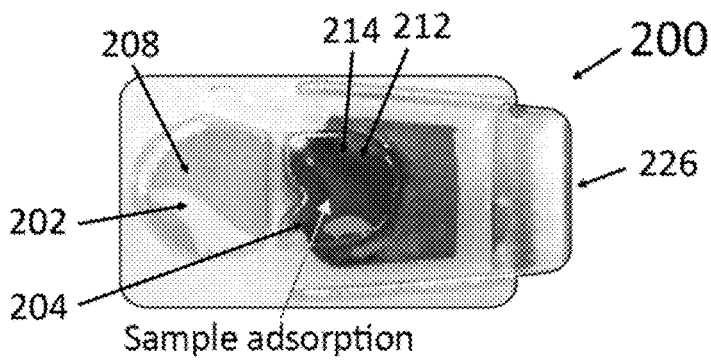
FIG. 2B is a top view of the device shown in FIG. 1B.
Figure 2C:
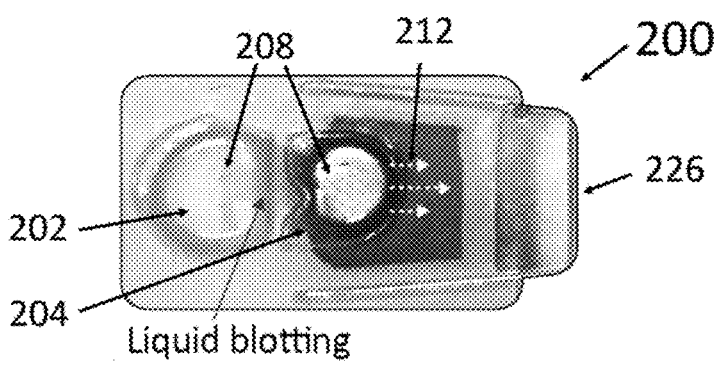
FIG. 2C is a top view of the device shown in FIG. 1C.
Figure 2D:
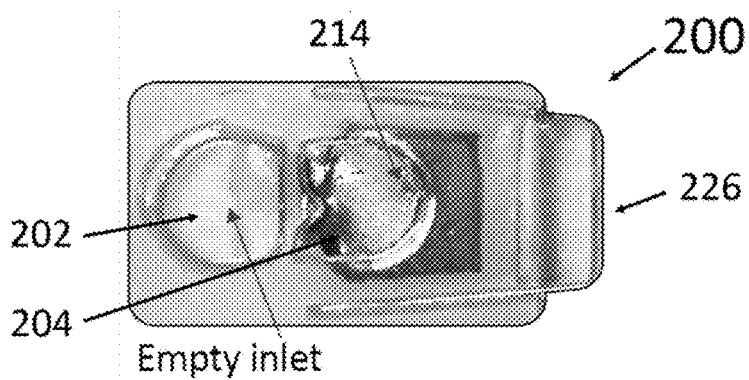
FIG. 2D is a top view of the device shown in FIG. 1D.

Once valve 220 is dissolved, excess amounts of both the sample liquid 210 and the stain liquid 208 are autonomously drained or blotted off by the two absorption units, blotting/filter papers 218 and 222, as shown in FIG. 1C. The particles 214 adhere to or are adsorbed by the grid 216. A remaining thin stain film 224 covers or embeds the particles 214 on the grid 216 and dries while the film 224 embeds the sample particles 214 (as shown in FIG. 1D). The grid 216 is then ready for imaging and can easily be retrieved by peeling off a flap 226 and extracting the grid 216 with, for example, a pair of tweezers.

FIGS. 2A-2D are top views of the device showing the corresponding frames.

Figure 3:
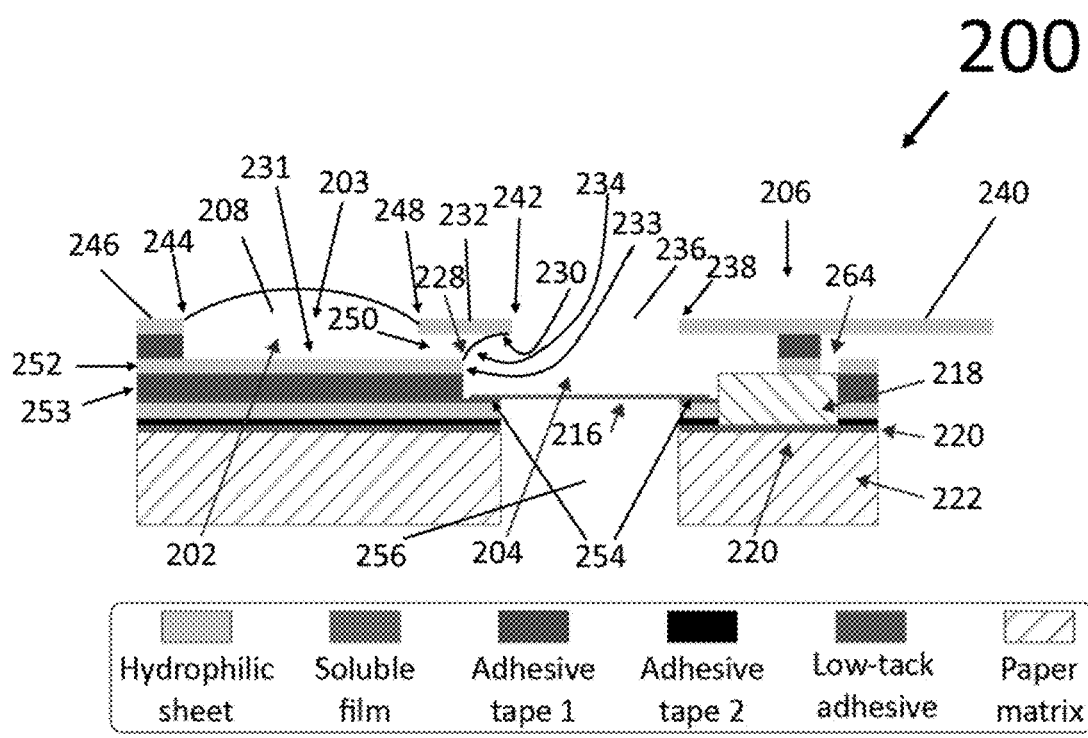
FIG. 3 is a schematic cross-sectional view of the device of the present invention.
Figure 4:
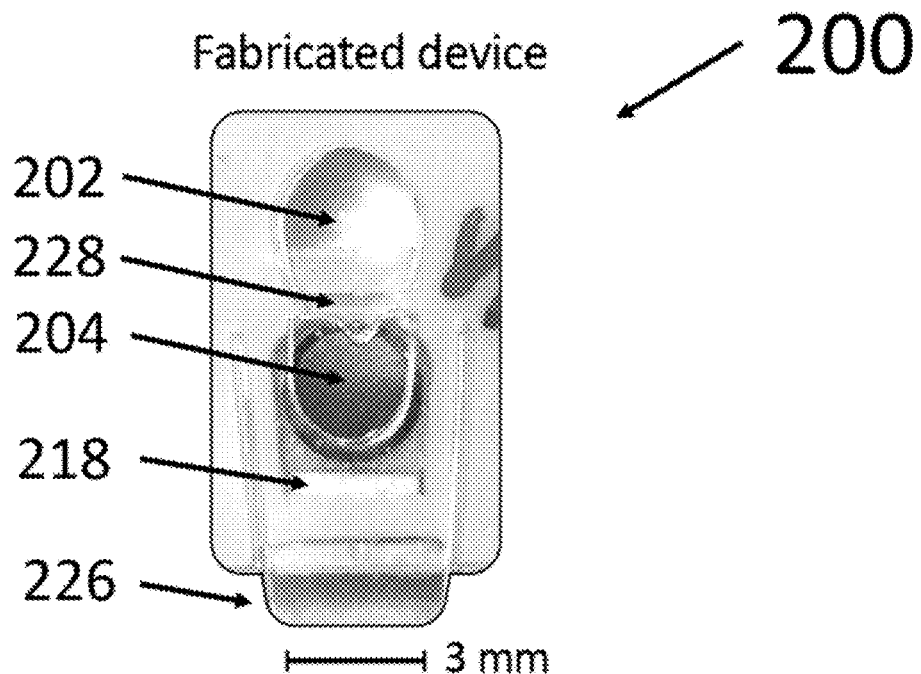
FIG. 4 is a schematic top view of the device shown in FIG. 3.
Figure 5:
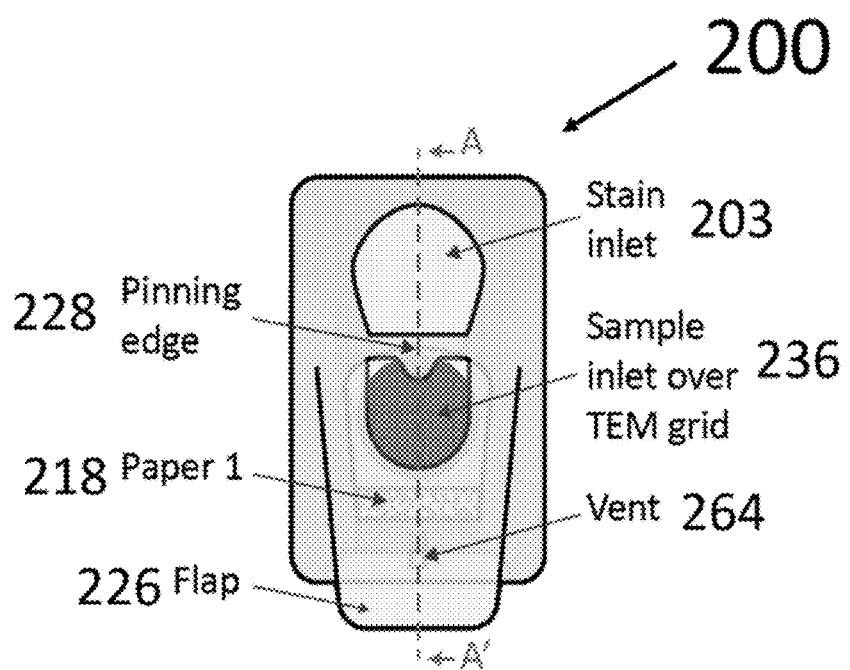
FIG. 5 is a top view of the device of the present invention.

The key components of the device 200 are depicted in the cross-sectional illustration shown in FIG. 3 and in the top view shown in FIG. 4. FIG. 5 shows a top view of a fabricated device of the present invention.

As indicated above, the microfluidic device 200 of the present invention consists of the liquid (stain) reservoir 202, the second liquid (sample) reservoir or grid chamber 204 and the draining unit 206. The key function of the stain reservoir 202 is to contain the stain liquid 208 until the user adds the sample liquid 210 that includes the particles 214 (best shown in FIGS. 1A-1D) that eventually come into contact with the stain liquid 208, as described in detail below.

A key enabling feature is a capillary stop valve or liquid pinning mechanism such as a pinning edge 228, as indicated in FIG. 3 that separates the stain reservoir 202 from the grid chamber 204. The capillary stop valve or mechanism could be a hydrophobic surface area and/or geometrical structure where surface tension prevents the liquid from going beyond the hydrophobic area and/or the geometrical structure. Preferably, the geometrical stop valve is a sudden divergence of the channel cross-section (e.g. an edge) in the flow direction of the channel or part of the channel. In the preferred embodiment, the capillary stop-valve is located the edge of the channel and ends where the second reservoir starts. It is not necessary to have a channel as long as there is an edge at the second reservoir that stops the first liquid from flowing into the second reservoir. If the edge had been located away from the second reservoir then there is a risk that an air bubble is formed between the first liquid and the second liquid so that no contact between the two liquids can be established. It is very important that the first liquid is easily accessible for the second liquid so that the two liquids can connect and the surface tension of the first liquid is broken.

One purpose of the liquid pinning mechanism of the present invention is to confine a liquid in one reservoir which is connected (in fluid communication) with a second reservoir. The stain liquid 208 is pinned at or held by the pinning edge 228 and is held to a hydrophilic underside 230 of a first laminate portion 232 due to surface tension forces between the stain liquid 208 and the underside 230.

Preferably, the pinning mechanism 228 is an edge, more particularly a sharp edge such as a 90-degree edge, formed between a horizontal bottom surface 231 and a vertical side wall 233 of laminate 252 that extends towards a laminate 253 and below the adhesive tape 254 holding the grid 216 in place. Surface tension at the surface 234 extending between the pinning edge 228 and the underside 230 holds the stain liquid 208 in place in the stain reservoir 202 and so that the surface 234 and the first laminate portion 232 extend over the pinning edge 228. The surface tension is caused by intermolecular forces near the surface leading to the apparent presence of a surface film and to capillarity on the surface. The surface of the liquid tends to contract and has properties resembling those of a stretched elastic membrane. The combination of the pinning edge 228, the hydrophilic underside 230 and the surface tension in the surface 234 thus enables the autonomous sample preparation process to be initiated by the addition of the sample liquid 210.

The grid chamber 204 has a sample inlet opening 236 defined between a forward edge 238 of a flap laminate 240 and a rearward edge 242 of the laminate portion 232. The stain reservoir 202 has an inlet opening 203 defined between a rearward edge 244 of a second laminate portion 246 and a forward edge 248 of the first laminate portion 232. Preferably, the first and second laminate portions 232, 246 and the flap laminate 240 are part of the same laminate to make the fabrication of the device 200 easier.

The grid chamber 204 contains the grid 216, such as TEM grid, and is connected to and in fluid communication with the stain reservoir 202 upstream of the grid 216. The grid chamber 204 is also connected to and in fluid communication with the draining unit 206 downstream of the grid 216. Preferably, the capillary forces drive the liquid sideways towards and into the draining unit 206. More particularly, the grid chamber 204 is in fluid communication with the stain reservoir 202 via a channel 250 defined between the laminate 232 and a bottom laminate 252 of the stain reservoir 202.

The grid 216 is fixated by a low-tack adhesive laminate 254 at the backside grid perimeter so that the grid 216 is removably held to the laminate 254. A cavity 256 is formed below the grid 216 to make sure that no liquid reaches the backside or underside of the grid 216 which otherwise could lead to TEM imaging artifacts.

The top or opening in the grid chamber 204 serves as the sample inlet 236 and ensures fast drying of the thin stain film after draining (blotting off) of excessive liquids. The opening 236 is slightly smaller than the length of the TEM grid 216 because the first laminate portion 232 and its rearward edge 242 extends over the grid 216. Similarly, the flap portion 240 and its forward edge 238 extend over the grid 216. This leaves an overlap between the top hydrophilic layer or laminate portions 232, 240 and the grid 216. The overlap ensures that the sample liquid 210 reliably connects with the preloaded stain liquid 208 and the draining unit 206.

The draining unit 206 is, preferably, formed by a stack of two absorption units or filter paper units 218 and 222 paper units and a water-soluble valve/membrane such as PVA film 220 that separates the two absorptions units or members 218, 222 from one another. The first and second absorption members could be any suitable porous matrix that provides good absorption of liquids such as paper i.e. cellulose but also cotton fibers, nitrocellulose and glass fibers. One function of the first or top absorption member 218 is to ensure a good contact between the draining unit and the second liquid in the second reservoir. One function of the second absorption member 222 is to ensure proper flow of the liquids from the first and second reservoir and into the second absorption member when the dissolvable membrane 220 has dissolved. Preferably, the two liquids flow in a sequence over the sample support or TEM grid 216 so that the sample liquid 210 flows over the sample support first and come in contact with the first absorption member 218 followed by the stain liquid 208 so that a portion of the stain liquid 208 remains on the sample support and embeds the substances or objects of the sample liquid 210. This principle applies to all the embodiments of the present invention even if the device only has one absorption member or the absorption member is located downstream of a dissolvable membrane such as a PVA film. PVA is especially suitable for the scope of the invention as biological specimens are typically prepared in aqueous solution. The top paper unit 218 provides a stable connection between the grid chamber 204 and the PVA layer 220. The paper unit 218 is in fluid communication with the sample reservoir or grid chamber 204. A vent 264, located above the top paper unit 218, ensures that no air is trapped which could block the draining process. The vent is an important feature when using a gas-tight membrane.

An important aspect of the present invention is that the dissolving time of the PVA layer 220 controls the adsorption time of the sample liquid 210 that has been deposited on the TEM grid 216. The draining or blotting step is triggered when the PVA layer 220 is dissolved by the liquid 210 of the sample and the liquid reaches the second absorption (paper) unit 222. The high capillary (draining) force of the second absorption (paper) unit 222 leads to fast absorption of the liquid volumes 210 and 208 contained in the device 200. After the sample preparation in complete, the flap portion 240 can be peeled off to collect the grid 216. Besides grid collection, the flap portion 240 could allow the user to introduce a grid of choice before the preparation procedure.

FIG. 5 is a top view of a fabricated version of the device 200 of the present invention.

Figure 6:
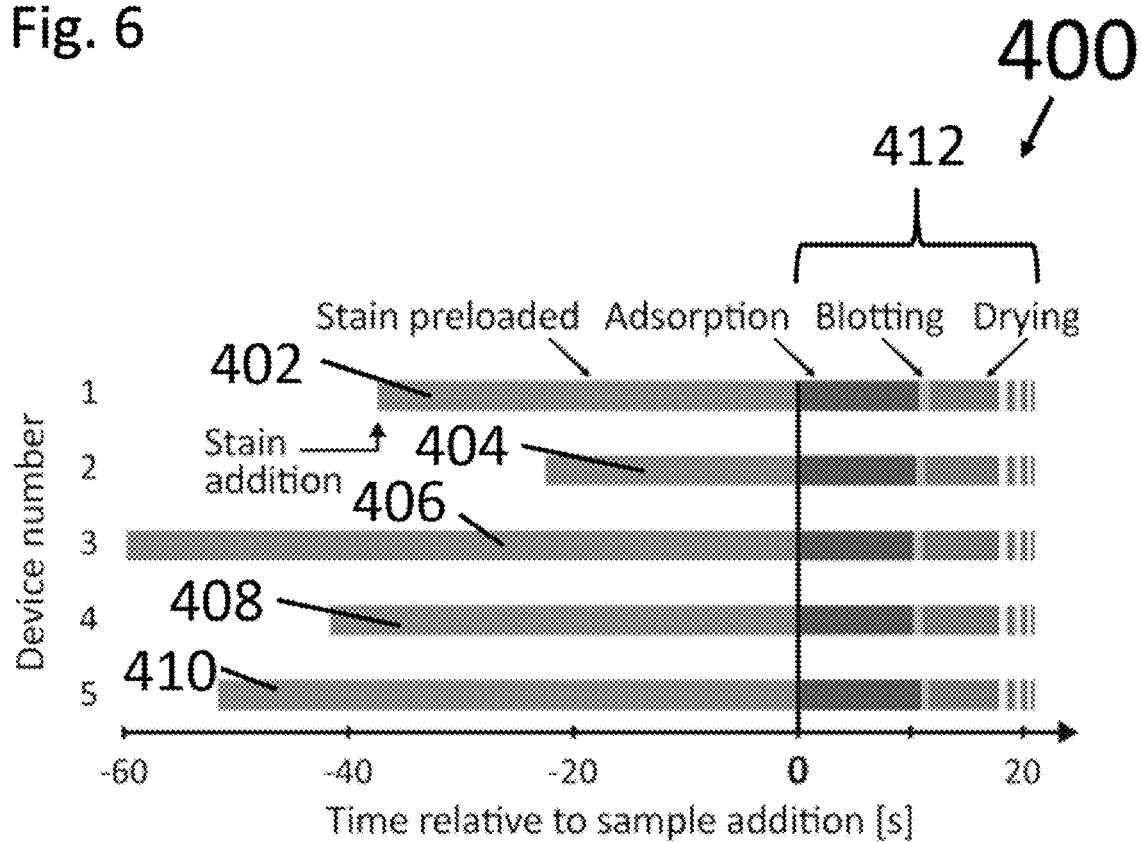
FIG. 6 is a schematic view showing microfluidic timing results for five different devices of the present invention.

FIG. 6 is a schematic view 400 showing test results of five different devices (device nos. 1-5) of the present invention. The view shows the preloading of stain at different times relative to the addition of the sample liquid containing the particles. More particularly, it shows the microfluidic timing results for five different devices and the times for stain preloaded, i.e. the time period between stain and sample addition, adsorption time, draining/blotting time and drying time of each device. The autonomous TEM grid preparation starts at time 0 with, and is triggered by, the sample addition, as described in detail above. The stain is added about 40 seconds before the sample addition (such as sample liquid 210) in device no. 1. The stain is added about 20 seconds before the sample addition in device no. 2, about 60 seconds in device no. 3, about 40 seconds in device no. 4 and about 50 seconds before the addition of the sample liquid in device no. 5. Although the time periods 402, 404, 406, 408, 410 for preloading the stain until the addition of the sample liquid vary between 20 seconds to 60 seconds, the time periods 412 to complete the adsorption, draining and drying steps are about the same for all five devices. The steps following the preloading step are all slightly longer than 20 seconds in total. The adsorption time period is thus the same as the time it takes for the sample liquid, absorbed in the first absorption media (such as paper), to dissolve the dissolvable membrane (PVA film). This means it is not time critical when the sample liquid is added relative to the time the stain was added or preloaded which makes the process easier for the user who adds the sample liquid.

Figure 7:
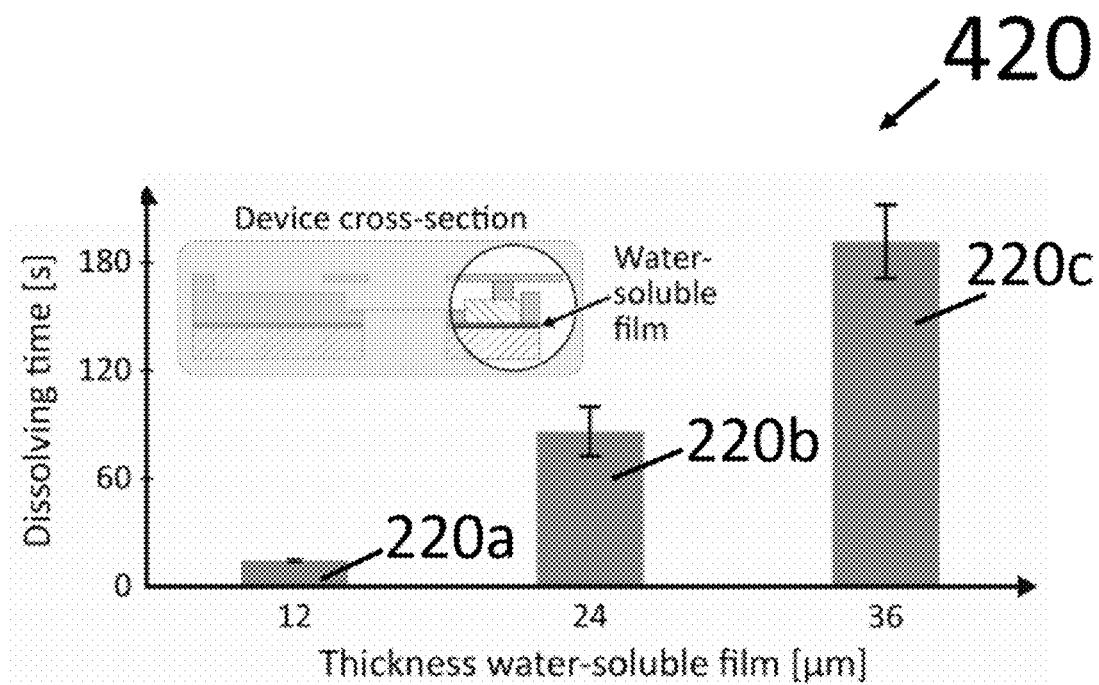
FIG. 7 is a schematic view illustrating measurement showing the average dissolving time of components of the present invention.

FIG. 7 is a schematic view 420 showing the time required to dissolve three different dissolvable membranes 220a, 220b, 220c having thicknesses 12 µm, 24 µm and 36 µm, respectively. Membrane 220a required about 15 seconds to dissolve, membrane 220b about 90 seconds and membrane 220c required over 180 seconds to dissolve.

Figure 8:
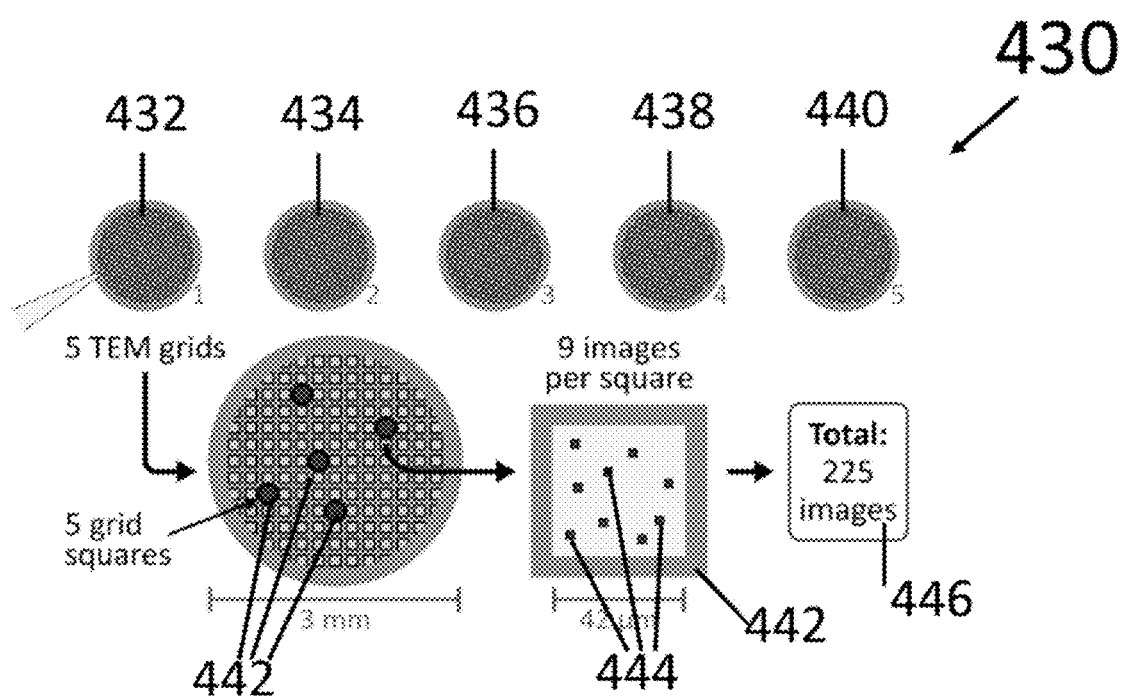
FIG. 8 is a schematic view illustrating five grids, five grid squares per grid and nine images per grid square results in 225 images of the present invention.

FIG. 8 is a schematic view 430 showing an imaging scheme with five grids 432, 434, 436, 438 and 440 with five grid squares 442 per grid and nine images 444 per grid square 442 that results in a total of 225 images 446.

Figure 9A:
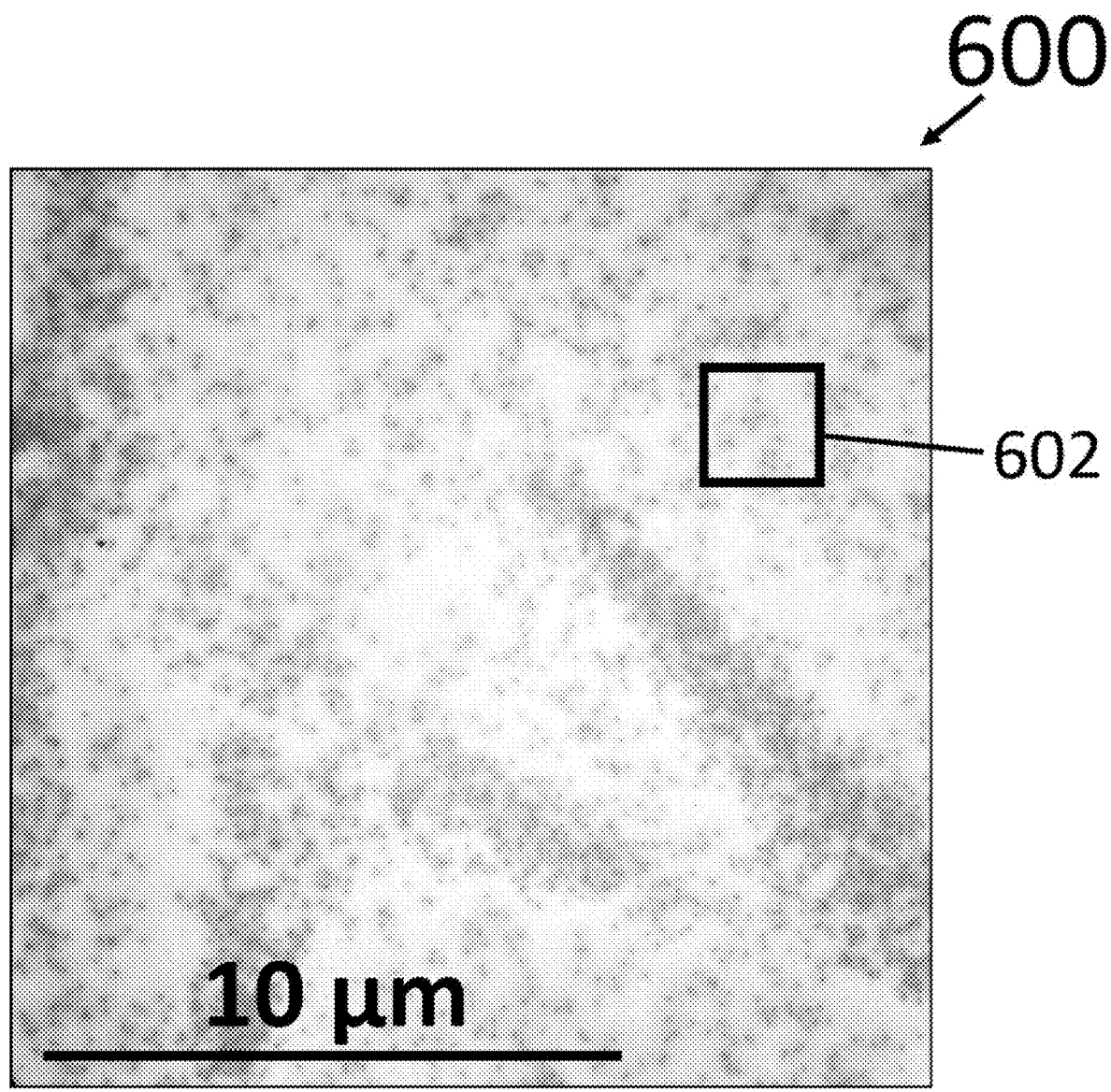
FIG. 9A is a magnified view of a TEM grid prepared by using the device of the present invention.
Figure 9B:
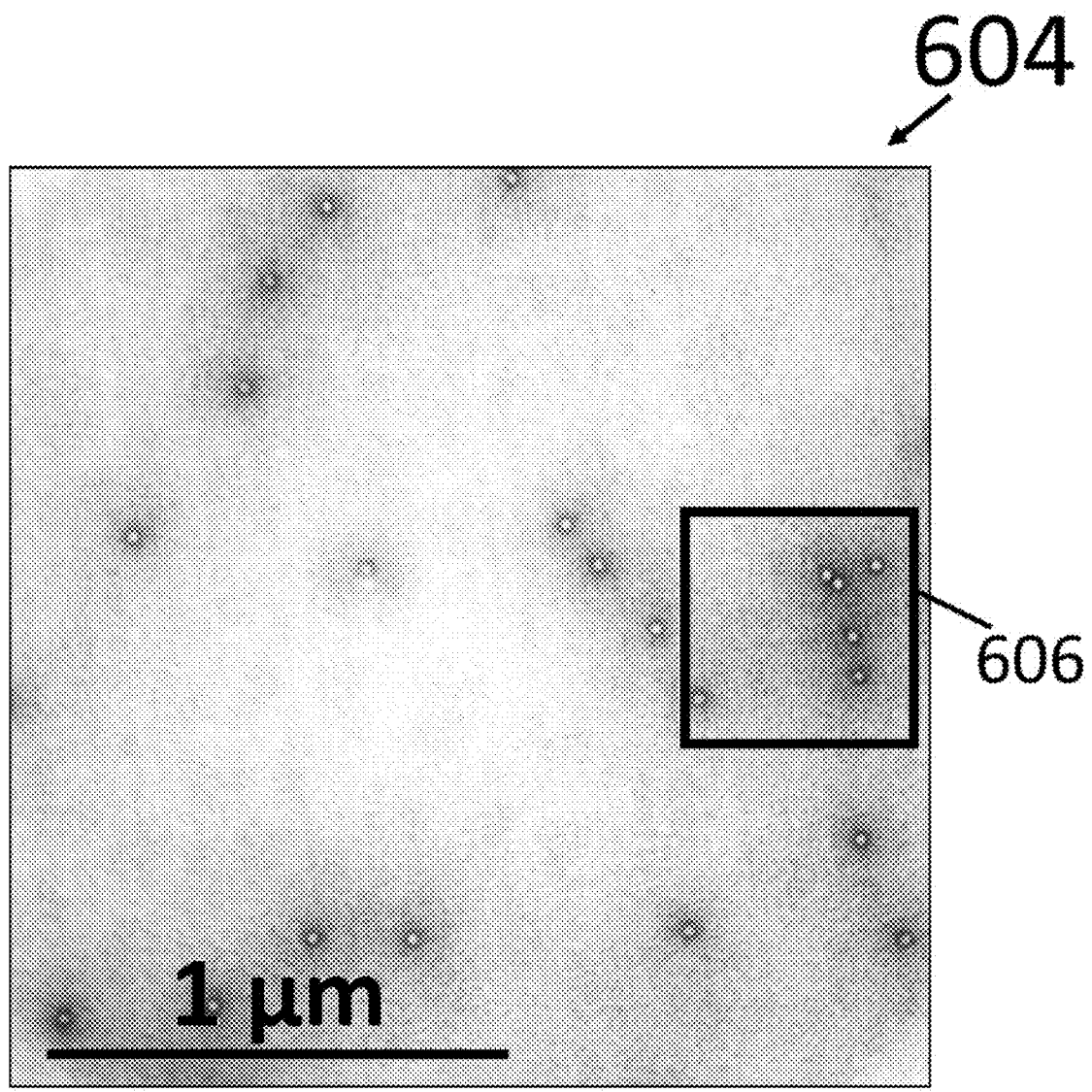
FIG. 9B is a magnified view of a sample area of the same size as the area marked in FIG. 9A.
Figure 9C:
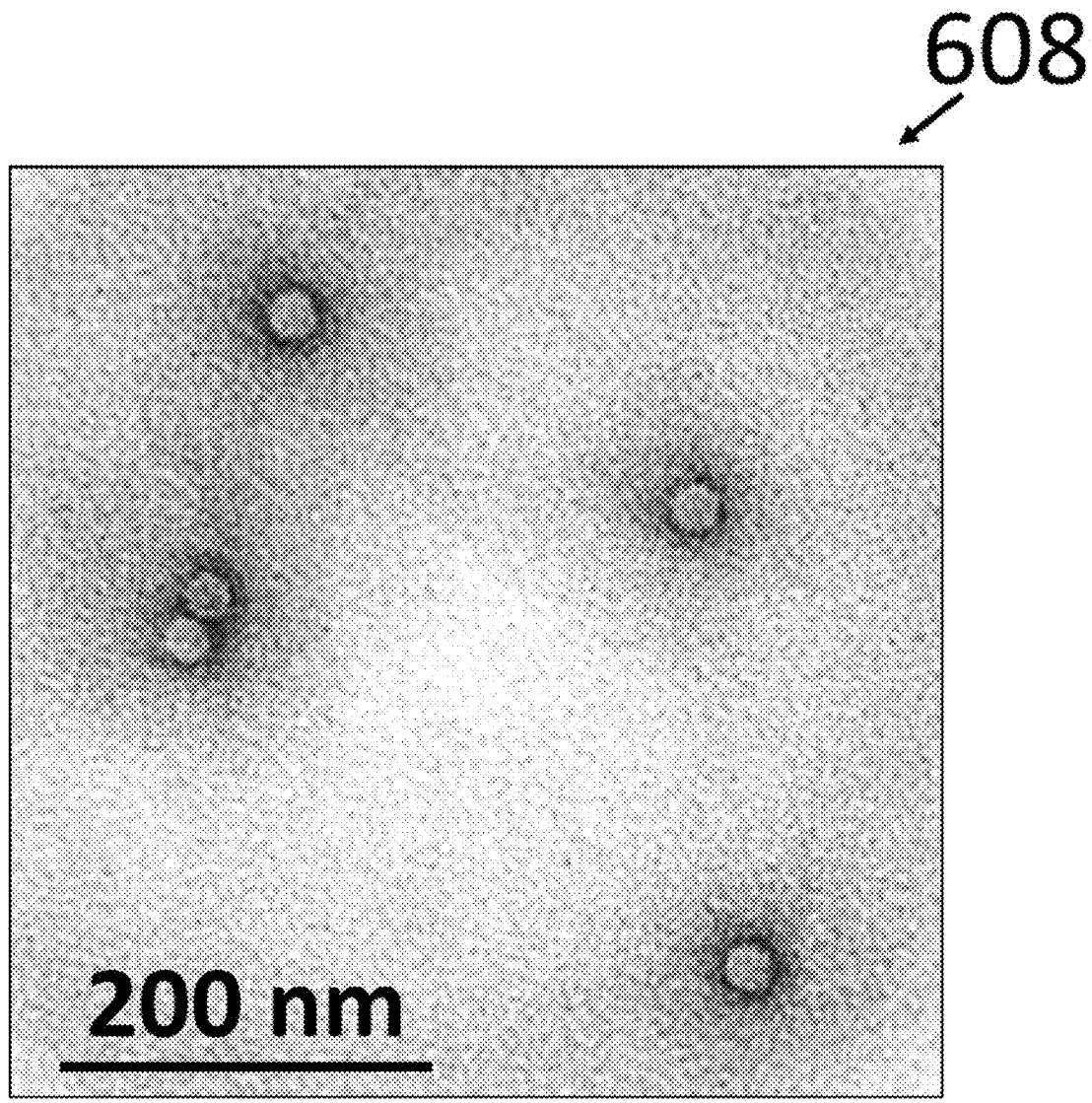
FIG. 9C is a magnified view of a sample area of the same size as the area marked in FIG. 9B.

FIG. 9A is an example magnified view 600, including a first portion 602, of a TEM grid prepared by the device of the present invention. FIG. 9B is a view 604, of higher magnification relative to view 600 in FIG. 9A, including a second portion 606, of the same size as the portion 602 marks in the view 600, shown in FIG. 9A. In the same way, FIG. 9C is a view 608, of higher magnification relative to view 604 in FIG. 9B, of the same size as the portion 606 of the view 604, shown in FIG. 9B.

Figure 10A:
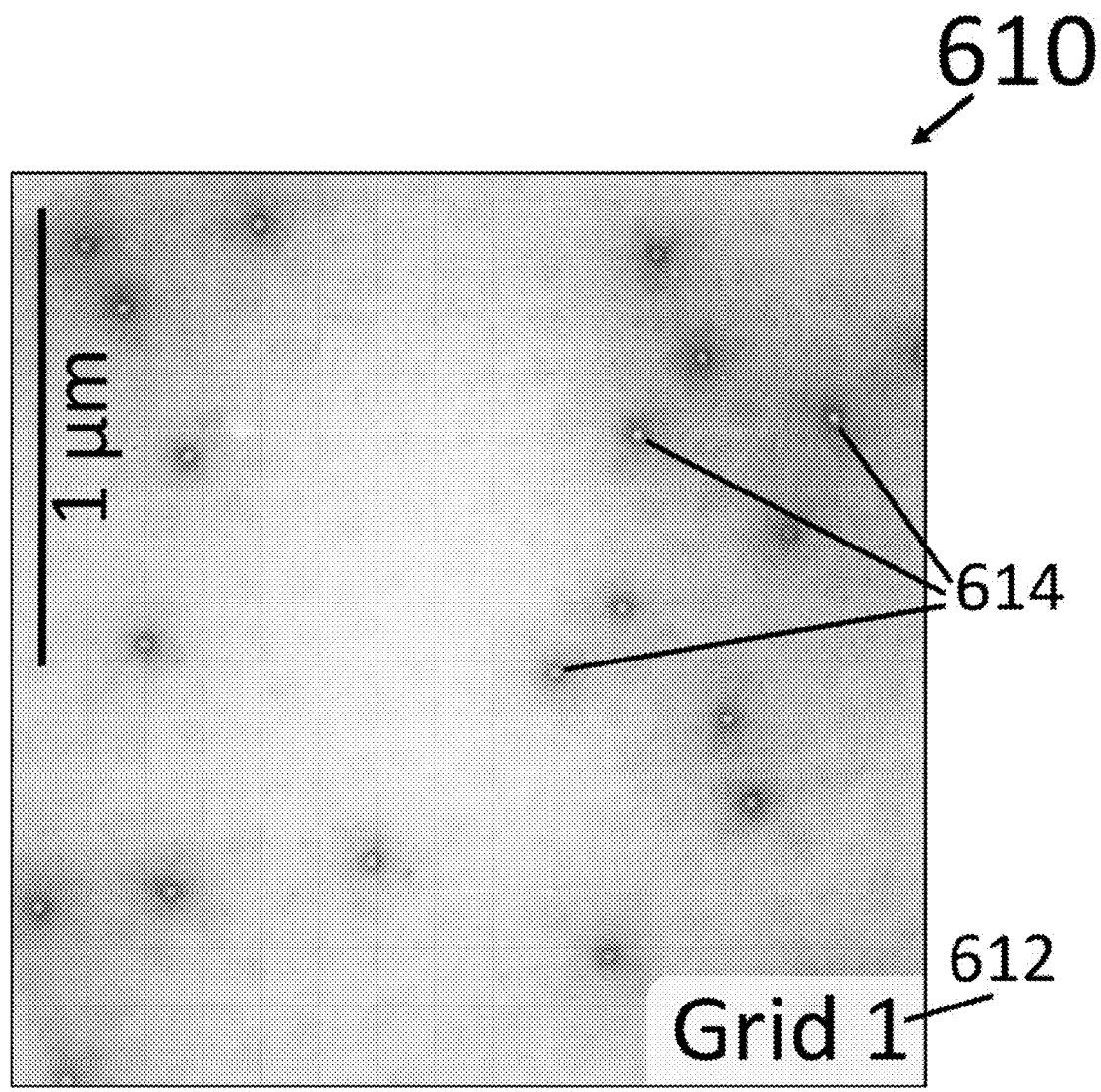
FIG. 10A is an example of an image from a first grid prepared by using the device of the present invention.
Figure 10B:
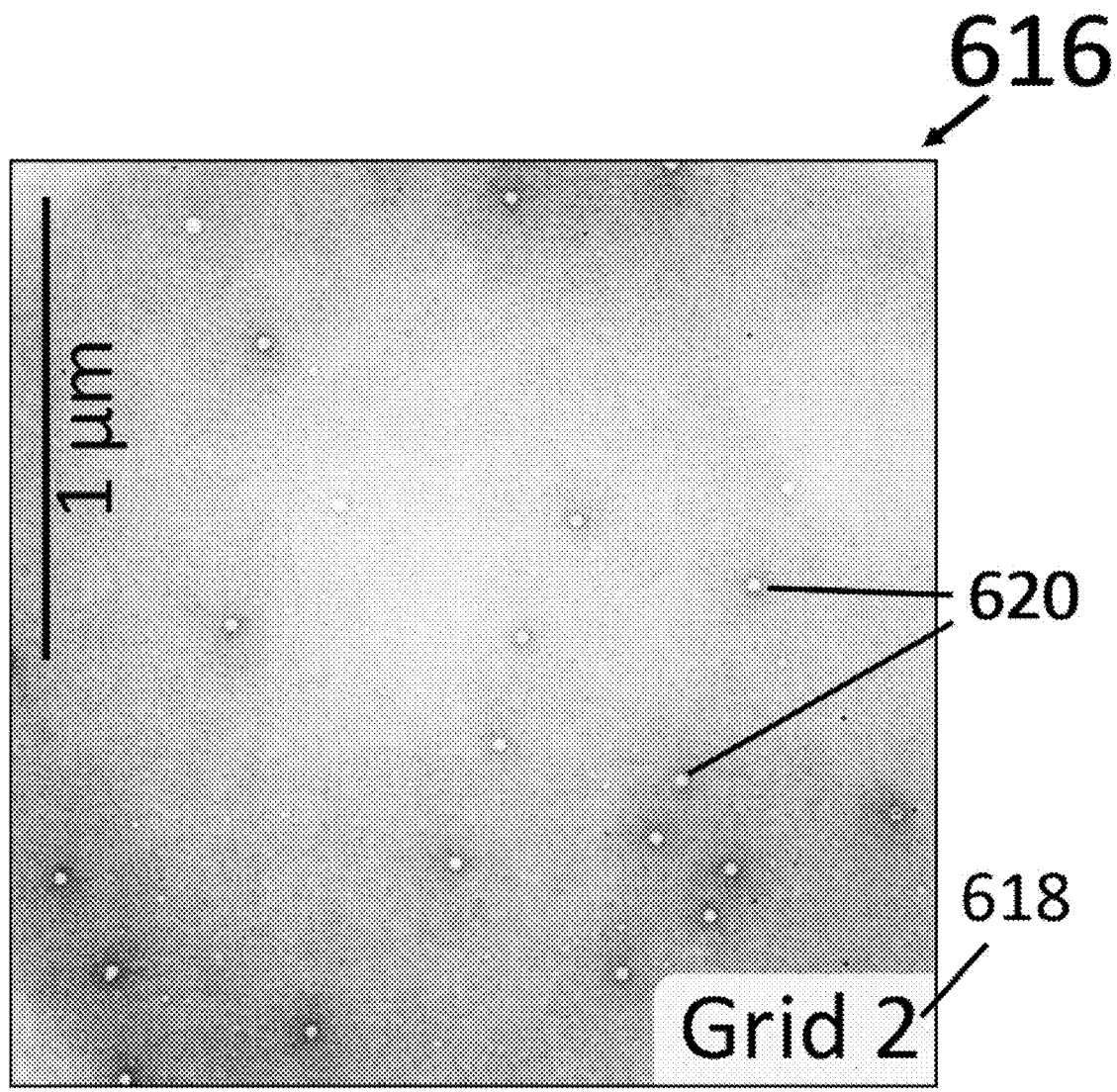
FIG. 10B is an example of an image from a second grid prepared by using the devoice of the present invention.
Figure 10C:
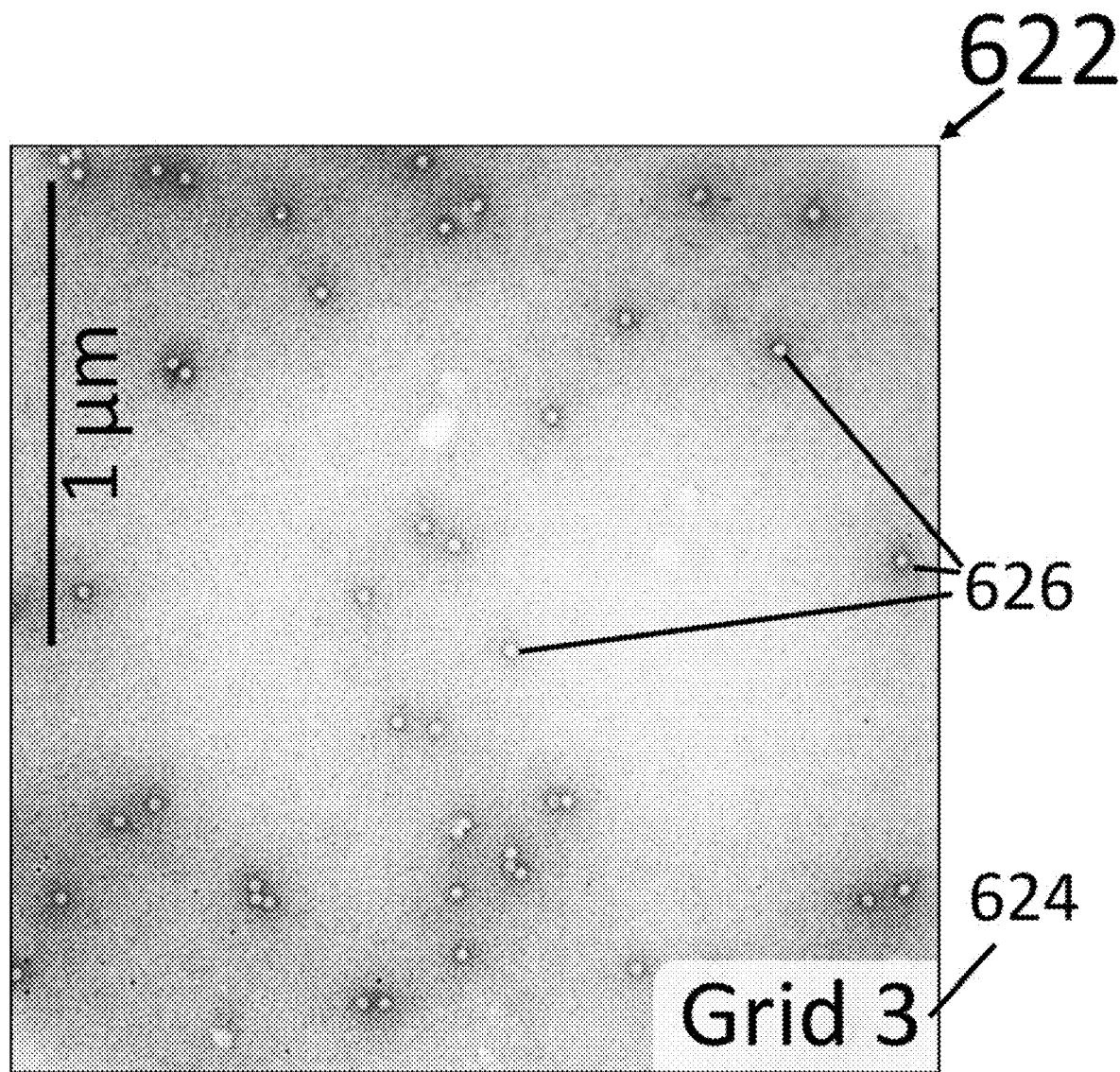
FIG. 10C is an example of an image from a third grid prepared by using the device of the present invention.
Figure 10D:
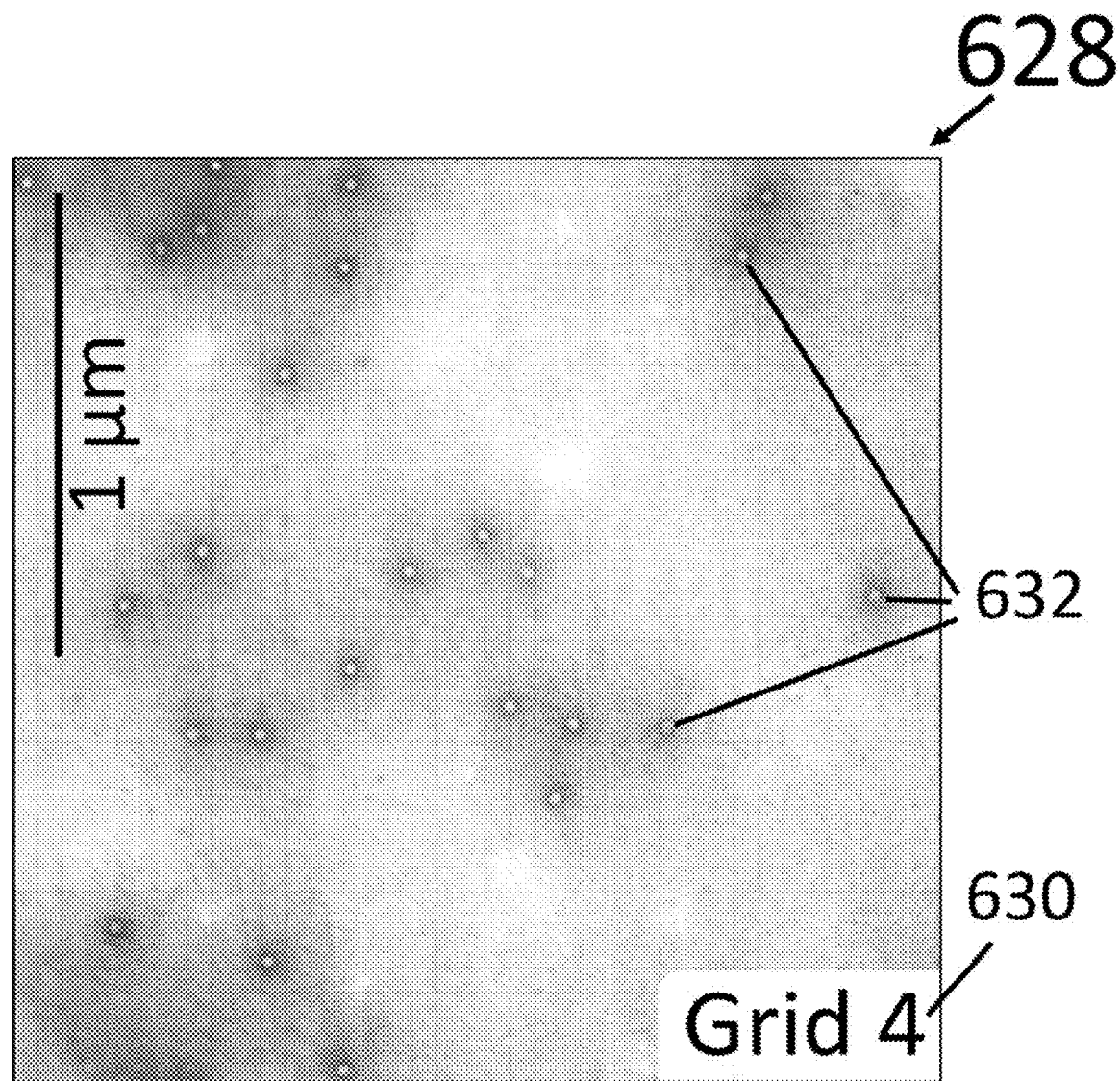
FIG. 10D is an example of an image from a fourth grid prepared by using the device of the present invention.
Figure 10E:
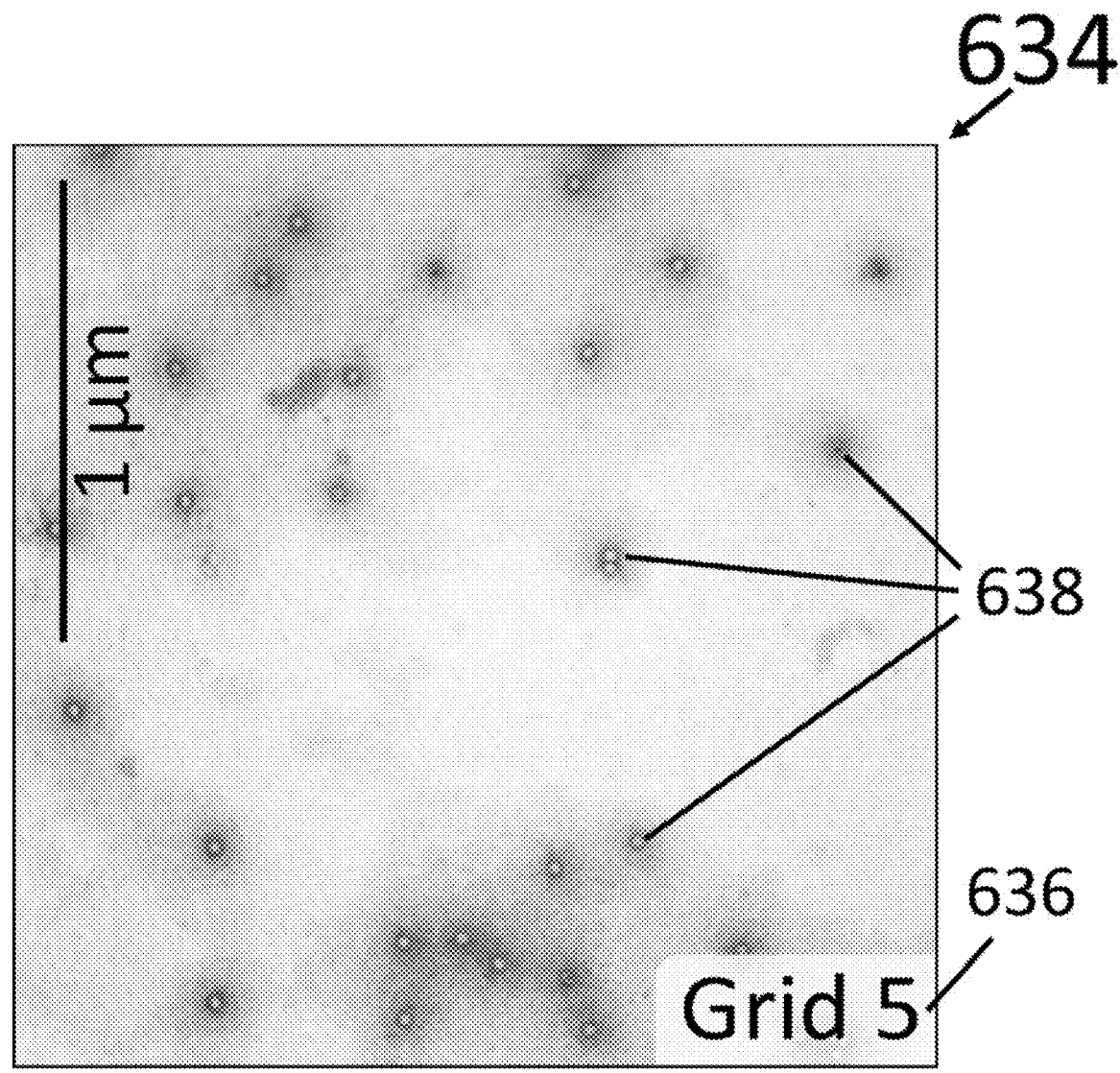
FIG. 10E is an example of an image from a fifth grid prepared by using the device of the present invention.

FIG. 10A is an example of an image 610 from a first grid 432, 612 that has been prepared by using the device and method of the present invention. The image 610 includes or depicts particles 614 such as virus particles. Similar to FIG. 10A, FIG. 10B is an example of an image 616 from a second grid 434, 618 that has been prepared by using the device and method of the present invention. The image 616 includes particles 620 such as virus particles. FIG. 10C is an example of an image 622 from a third grid 436, 624 that has been prepared by using the device and method of the present invention. The image 622 includes particles 626 such as virus particles. FIG. 10D is an example of an image 628 from a fourth grid 438, 630 that has been prepared by using the device and method of the present invention. The image 628 includes or depicts particles 632. FIG. 10E is an example of an image 634 from a fifth grid 440, 636 that has been prepared by using the device and method of the present invention. The image 634 includes or depicts particles 638 such as virus particles or any other suitable particle.

Figures 11, 12:
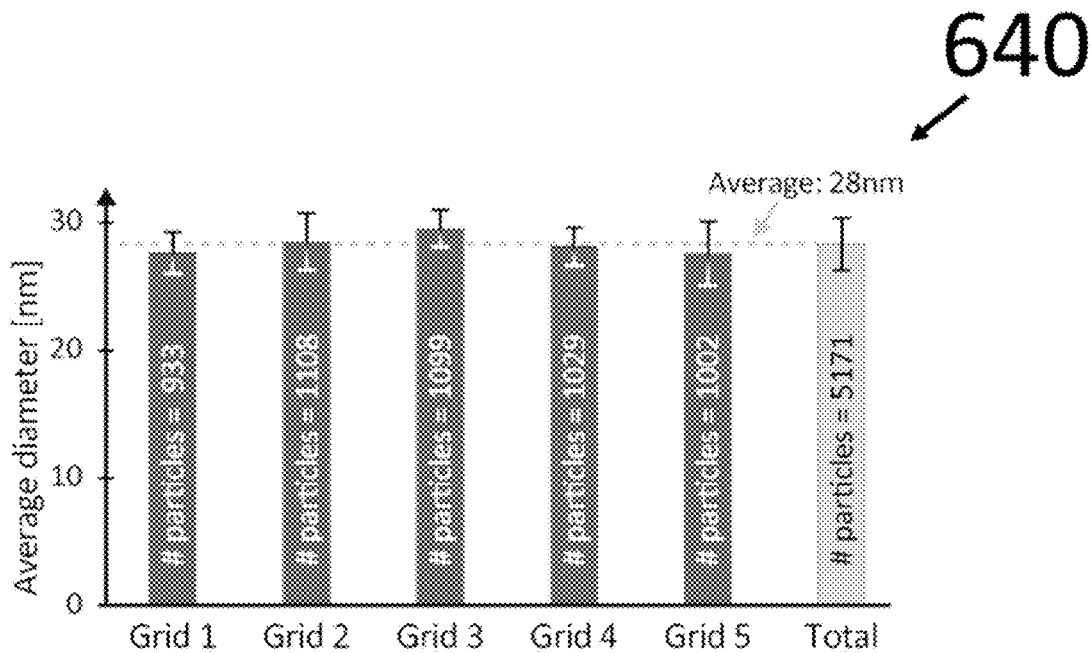
FIG. 11 is a schematic illustration of the average diameter of the particles and the number of particles on each grid of the present invention.
FIG. 12 is a table showing results of a manual subset testing with five images per grid and the ratio of true and false positives.
Figure 13:
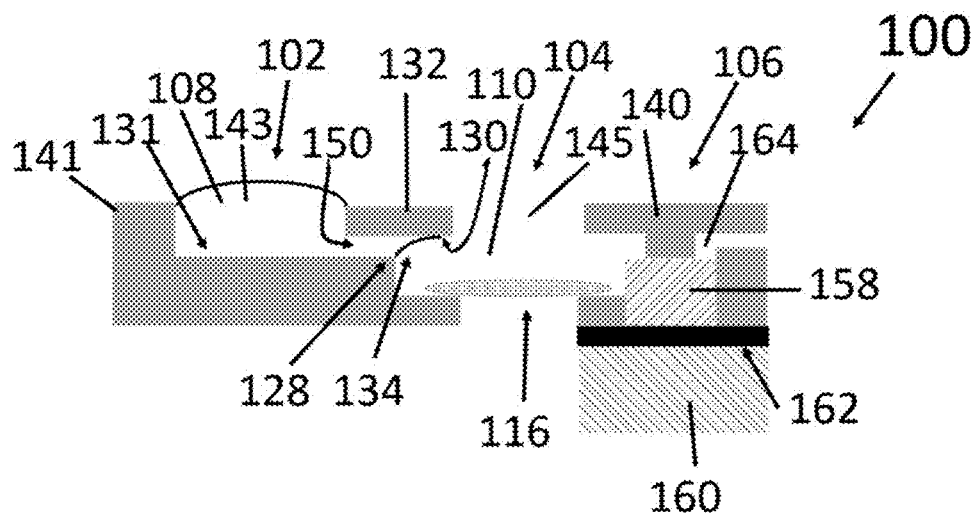
FIG. 13 is a schematic cross-sectional view of the device of the present invention.

FIG. 11 is a graph 640 of the average diameter of the particles and the number of particles on each grid that has been prepared by using the device and method of the present invention;

FIG. 12 is a table 642 showing results of a manual subset testing with five images per grid and the ratio of true and false positives;

FIG. 13 is a cross-sectional view of the microfluidic device 100 of the present invention. It should be noted that the device 100 is not fabricated from laminates. The device 100 is substantially similar to device 200 and everything that applies to device 100 also applies to device 200 and vice versa. The device 100 has a microfluidic platform with liquid reservoirs in fluid communication, and absorption units and a dissolvable film that act as time-controlled liquid drainage with a delay valve. The sample support 116, here illustrated as a TEM grid, is positioned at a bottom of the sample reservoir 104. The stain reservoir 102 has an inlet opening 143 defined between the front end of a back section 141 of the device and the back end of a middle section 132 of the device. Preferably, if the device is constructed using laminate technology, the sections 140, 132 and 141 are part of the same laminate which makes it easier to fabricate the device 100

The sample reservoir 104 has an inlet opening 145 defined between the laminate or section 132 and the laminate or section 140. The sample reservoir 104 is upstream (on one side) connected to and in fluid communication with a stain reservoir 102 via a microfluidic channel 150 that extends between the sample reservoir 104 and the upstream stain reservoir 102. It is to be understood that the channel 150 may have a pinning edge or a discontinuity at only a portion of the end of the channel 150 so that, for example, the sidewalls do not have any edges. There may also be an edge of the channel at the upper side of inner surface so that there are two opposite edges at the end of the channel.

Preferably, the channel 150 is defined between a hydrophilic underside 130 of a first laminate portion or section 132 and a bottom surface 131 of the stain reservoir 102. The bottom surface 131 extends to a pinning edge 128. Capillary forces between the liquid 108 and the underside 130 and the surface tension of the surface 134 hold the liquid 108 in the stain reservoir 102 and prevents the liquid 108 from flowing into the sample reservoir 104. In other words, the pinning edge 128 prevents liquid 108, such as stain liquid, added to the stain reservoir 102 from flowing into the sample reservoir 104.

The sample reservoir 104 is downstream (on the opposite side relative to the upstream connection to the stain reservoir 102) connected to and in fluid communication with a first filter or absorption media 158 which is separated from a second filter or absorption media 160 by a dissolvable film, membrane or valve 162. The first filter 158 is also connected to a vent 164. The vent 164 serves as an emergency exit for potentially trapped air and gas which would otherwise hinder the flow of the liquid 108, 110 into and to be absorbed by the first and second filters 158, 160.

Figure 14:
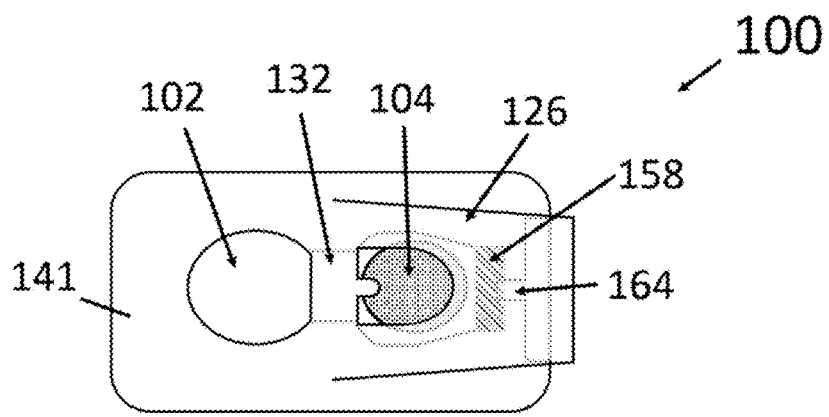
FIG. 14 is a top view of the device shown in FIG. 13.

With reference to FIG. 14, the removable flap 126 is, upon completion of the grid preparation, removed from the device 100 prior to removing the sample grid 116 from the sample reservoir 102.

Figure 15:
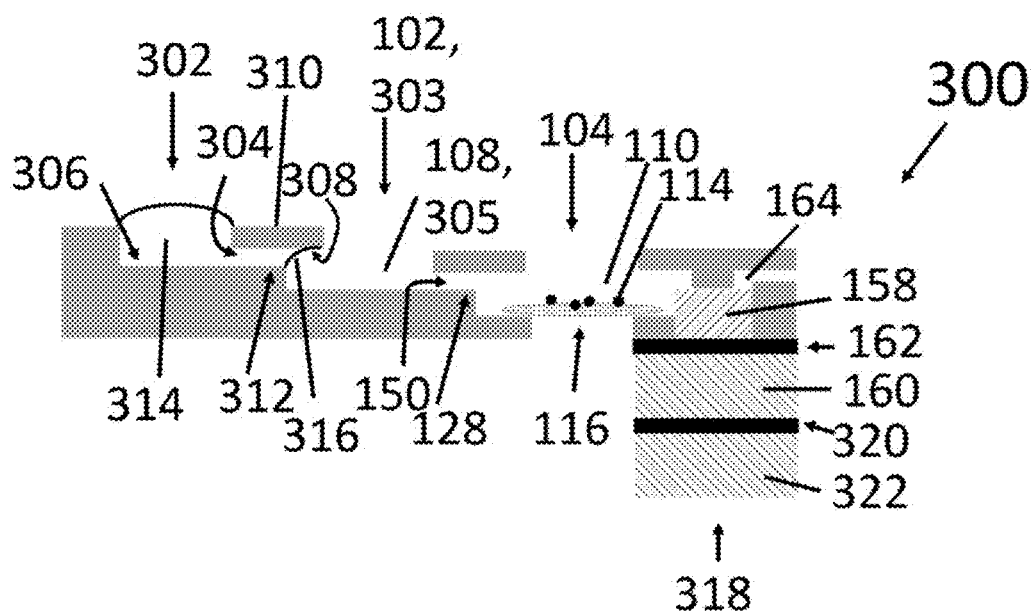
FIG. 15 is a cross-sectional side view of a first alternative embodiment of the device of the present invention.

FIG. 15 shows a device 300 that is substantially similar to the device 100 shown in FIG. 13 but includes an additional reservoir 302 and an additional dissolvable film or membrane or valve 320 and an additional absorption unit 322. Only the main differences between device 100 and device 300 are here described. The device 300 is used when additional liquids are to be flushed over the grid 116 in a sequential and time-controlled manner. The additional liquid reservoir 302 is placed upstream of the stain or second reservoir 102 and in fluid communication with and connected thereto via a channel 304 that is defined between a bottom surface 306 of the reservoir 302 and a hydrophilic underside 308 of a laminate portion or section 310. Between the reservoirs 302 and 102, there is a second pinning edge 312 that prevents liquid 314 in the upstream reservoir 302 from flowing into the stain reservoir 102, 303. The liquid 314 is held in place in the reservoir 302 in the same way as the liquid 108 in the reservoir 102 i.e. by capillary forces to the hydrophilic underside 308 and by surface tension in the surface 316.

The order of the reservoirs corresponds to the order in which the liquids flow over the grid 116. That is, if the liquids are sample, wash, stain then the stain liquid should be added to the upstream reservoir 302. The wash liquid should be added to the middle or second reservoir 102, which upon addition connects to the liquid in the upstream reservoirs 302. The sample liquid should be added to the first reservoir 104 on top the grid 116, which upon addition connects to the upstream liquid train of wash 305 and stain 314 and downstream connects to the draining unit 318.

The draining unit 318 has the absorption members (filter papers) 158, 160 and dissolvable film 162 and is located downstream of the sample reservoir 104. The draining unit 318 has an additional dissolvable film 320 and another filter or absorption member 322 to illustrate how the timing of the additional liquid can be controlled. The thickness of the first dissolvable film 158 decides how long the first liquid 110 added to the sample reservoir 104 sits or stays on top of the grid 116 i.e. how long the sample liquid 110 and particles 114 are permitted to adhere to the grid 116. The second filter 160 should be big enough to absorb and store the amount of liquid corresponding to the volume of the sample liquid 110. Once the liquid 110 reaches the second dissolvable film or membrane 320, the flow of the liquid over the grid 116 stops until the film 320 has been dissolved and the last filter 322 in this setup with 3 liquids pulls the second liquid 108, 305 and third liquid 314 over the grid 116 by absorbing all the volumes of all three liquids 110, 108/305 and 314.

Figure 16:
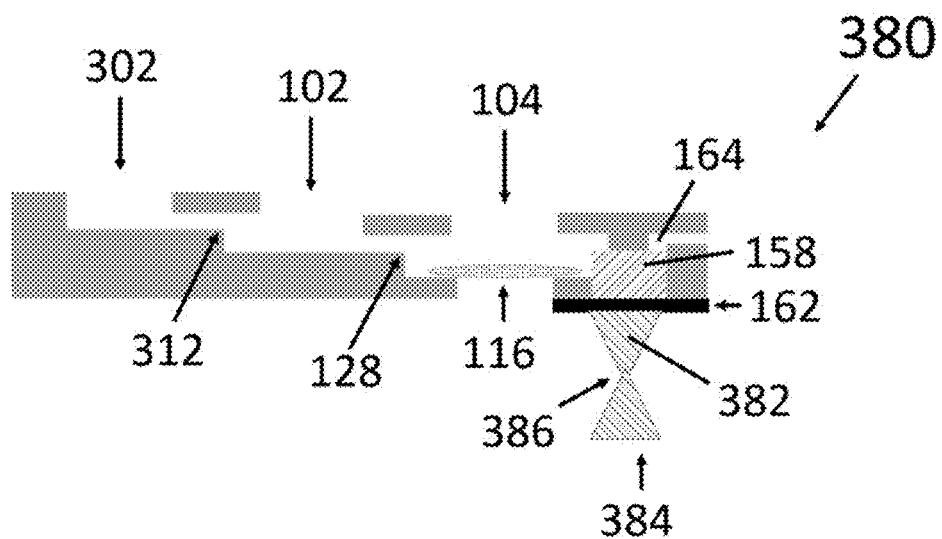
FIG. 16 is a cross-sectional side view of a second alternative embodiment of the device of the present invention.

FIG. 16 shows a device 380 which includes modifications of the devices shown in FIGS. 13 and 15 and illustrates how the shapes of the filter paper 382 in the draining unit 384 can be modified in order to steer the flow-speed of the liquids. Everything else in device 380 is identical to the components of devices 100 and 300. A narrow and thin filter paper or the filter paper 382 with a neck 386 slows down the flow speed over the grid 116 whereas a wide and thick filter increases the flow speed.

Figure 18:
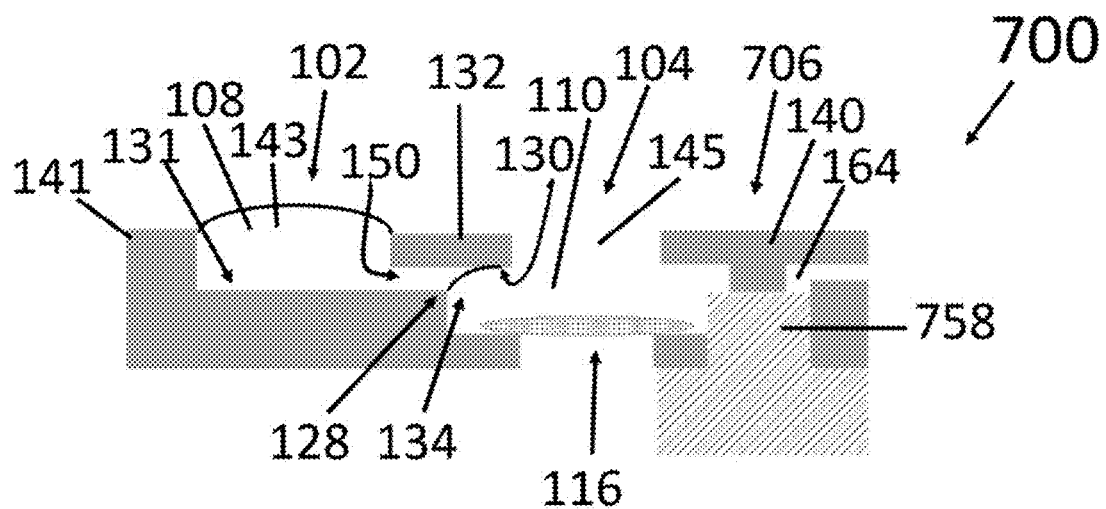
FIG. 18 is an elevational schematic cross-sectional view of a fourth alternative embodiment of the device of the present invention.
Figure 19:
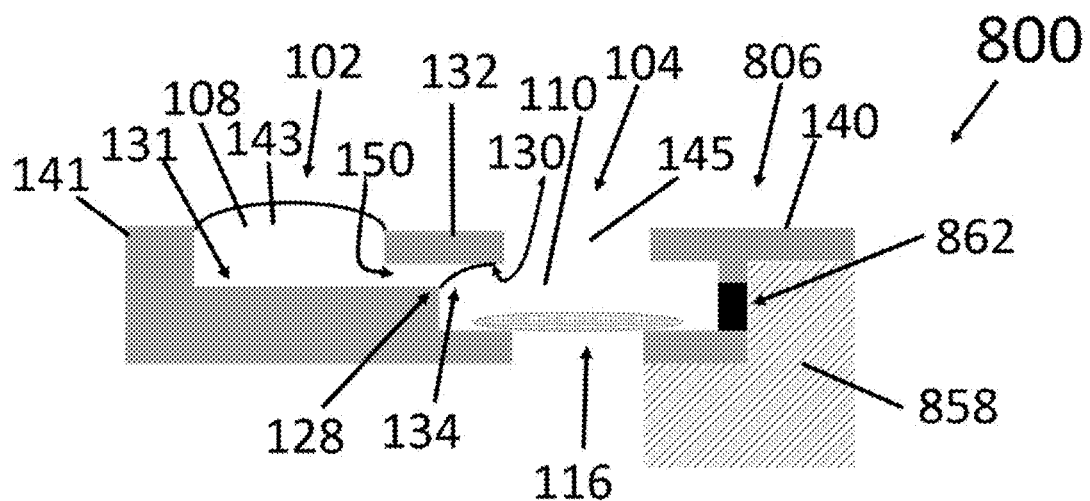
FIG. 19 is an elevational schematic cross-sectional view of a fifth alternative embodiment of the device of the present invention.

FIGS. 18-19 show alternative embodiments of the devices 700, 800, respectively, that are virtually identical to device 100 shown in FIG. 13 except that the draining or blotting units 706, 806, respectively, are different from draining or blotting unit 106. Preferably, draining unit 706 has only one first absorption member 758 but no dissolvable membrane or a second absorption member, as shown in FIG. 13. The operation of device 700 is substantially similar to that of device 100 in that the liquids in the first and second reservoirs are absorbed by the absorbing member 758 during a suitable time period so that there is enough time for the particles in the sample liquid to adhere to the grid 116, as explained in detail with reference to devices 100, 200.

Similarly, device 800 is substantially similar to that of device 100 except that the draining unit 806 has a dissolvable membrane 862 and a first absorption member 858. The draining unit 806 does not have an absorption member between the dissolvable membrane 862 and the second reservoir 104 so that the dissolvable member 862 comes into direct contact with the second liquid without the second liquid having to pass through an absorption member before coming into contact with the dissolvable member to start dissolving the dissolvable membrane 862. Except for the differences of the draining units 706, 806 compared to draining unit 106 all other features and method steps of devices 700, 800 are the same as devices 100, 200 described in detail above.

Figure 20:
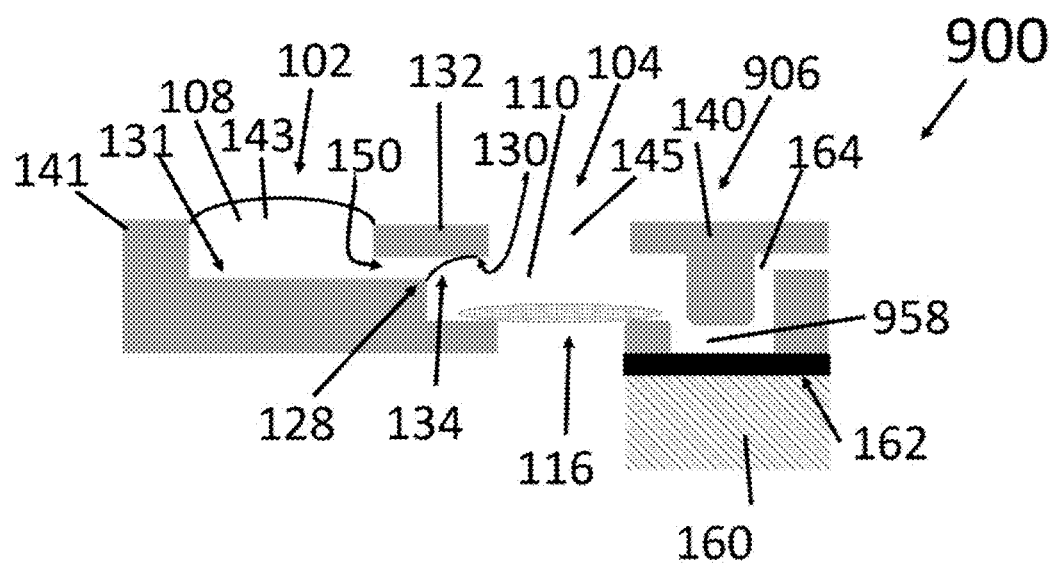
FIG. 20 is a cross-sectional view of a sixth alternative embodiment of the device of the present invention.

FIG. 20 is yet another embodiment of the device 900 that is substantially similar to the device 100 shown in FIG. 13 except that it has a capillary channel 958 in draining or blotting unit 906 instead of the first absorption member 158. The capillary forces in the channel 958 urges the second liquid 110 from the second reservoir 104 into the channel 958 so that the liquid 110 comes into contact with the dissolvable membrane 162 to dissolve the membrane, as described in detail in connection with devices 100 and 200.

In operation, the method of the present invention comprises the steps of providing the stain reservoir 202 connected to and in fluid communication with the grid chamber or sample liquid reservoir 204 that has a pre-mounted grid 216. The reservoir 204 is in turn connected to, and in fluid communication with, the draining unit 206. The stain liquid 208 is added to the stain reservoir 202 which is contained in the reservoir 202 until the user adds the sample liquid 210 including the particles 214 into the sample liquid reservoir 204.

This key feature is enabled through a capillary stop valve or pinning mechanism, here in the form of an edge 228 located at the end of channel 250 that separates the stain reservoir 202 from the grid chamber 204. The stain liquid 208 is pinned at the pinning edge 228 due to capillary forces so that the liquid 208 adheres to the underside 230 and extends over the pinning edge 228 and the surface tension at the surface 234 prevents the liquid 208 from flowing into the grid chamber 204 although there is fluid communication between the stain reservoir 202 and the sample reservoir or grid chamber 204 via channel 250. The fact that the stain liquid 208 is held inside the stain reservoir 202 in this way enables the sample preparation process to be initiated by adding the sample liquid 210 including the particles 214 into the sample reservoir 204. The liquid 210 is added in such an amount so that the liquid 210 comes into contact with surface 234 to break the surface tension of the liquid 208 between the pinning edge 228 and the underside 230. When the surface tension of the surface 234 is broken, the two liquids 210, 208 are connected with only minor mixing of the liquids at the interface. When the sample liquid 210 including the particles 214 are added to the grid chamber 204 via the opening 236 from above the device 200, the liquid 210 also flows into and connects with the draining unit 206 that is downstream of the sample reservoir 204. The opening 236 through which the sample liquid 210 and particles 214 are added is slightly smaller than the width of the grid 216 to make the sample liquid 210 reliably connects to the stain liquid 208 and the blotting unit 206. The cavity 257 located below the grid 216 makes sure that no liquid flows and attaches to the wrong side of the grid 216 and interferes with the quality of the preparation.

The draining unit 206 has two absorption units (such as filter papers) 218 and 222 and the soluble PVA film 220 located between the two filters 218, 222. The top filter 218 makes sure that the sample liquid 210 reliably connects to the PVA film 220 by absorbing the liquid 210 so that the liquid travels from a top side of the filter 218 to a bottom of the filter 218 that is in contact with the dissolvable film 220.

The vent 264 above the top filter serves as the emergency exit for potentially trapped air, which could otherwise block the connection between the sample liquid 210 and the draining unit 206. The sample liquid 210 flows through the top filter 218 and upon contact with the PVA film or layer 220 dissolves the PVA layer 220 so that the liquid can flow into the filter 222 located below the filter 218. The time is takes for the sample liquid 210 to dissolve the PVA layer 220 is critical because it controls the time the particles 214 in the sample liquid 210 are permitted to adhere to and adsorb into the grid 216. Once the PVA layer 220 is dissolved, the liquid 210 followed by flow into and connect to the bottom filter 222 which absorbs all the liquid 210, 208 in the device 200. The filter or absorption member 222 first absorbs the sample liquid 210 and then the stain liquid 208. The bottom filter 222 hence corresponds to the manual blotting step. The opening 236 over the grid 216 through which the sample liquid 210 and the particles 214 were added, now ensures rapid drying of the thin stain film 224 that remains left after the draining/blotting by the two absorption members or filters 218, 222 have absorbed all excess liquid 210, 208. Finally, the flap 226 can be peeled off the device 200 to provide easy access to the grid 216 that is easily extracted from the device 200 for subsequent imaging in, for example, a ns-TEM device.

If more liquids need to be added in a sequential manner, for example a washing liquid 305 in a washing step before the stain liquid 314 is added to the sample liquid 110, another liquid reservoir 302 connected to and in fluid communication with the middle reservoir 303 via the channel 304 and separated by the pinning edge 312 can be added, as shown and described in connection with FIG. 15. The wash liquid 305 should then be added to the middle reservoir 303 after the stain liquid 314 is added to the most upstream reservoir 302. If the incubation time of the additional liquid (here the wash liquid 305) need to be controlled, an additional layer of soluble film 320 and filter paper 322 can be added to the draining unit 318.

The speed of the flow over the grid 116 can be controlled by the shapes and thicknesses of the filter papers in the draining unit. Less amount of available absorption media (i.e. filter/paper) or lower capillarity (also known as Wicking rate) of the filter results in a slower flow/drainage and vice versa. For example: a thin, narrow and long filter after the soluble film results in a slower liquid flow and drainage pace.

Instead of adding a droplet of a pre-mixed stain solution, the salt constituting the stain can be dried at the bottom of the stain reservoir 102 and then only water or another dissolvent/buffer is added to the reservoir 102 when preparing the stain reservoir and the grid. The stain salt is then dissolved when the dissolvent is added to create the stain liquid 208.

Instead of adding a hydrophilized grid to the preparation assembly kit, a hydrophilization liquid such as Alcian-Blue can be flushed over the grid before the sample liquid is added. In this way, the stain and sample liquids are loaded in two separate reservoirs upstream of the grid chambers 102 and 302, (best shown in FIG. 15) connected via microfluidic channels 304 and 150 but kept separate via pinning edges 128 and 312. The grid hydrophilization liquid is then added directly onto the grid 116 in the grid chamber 104 to start the sequence of liquids flowing over the grid 116, i.e., initiating the grid preparation process.

An alternative use of the method of the present invention is to use it for controlled deposition of a matrix on top of the grid 116. The same method as described above applies with the exception that only one liquid, i.e. the substrate, is used and it is added to the grid chamber 104. For example, fibers, such as spider silk, may be permitted to polymerize in the air-liquid interface on the droplet of the sample (substrate) added onto the grid 116. When the soluble layer 162 is dissolved, the spider silk gently falls down on the EM grid while the filter paper 160 drains the device. The fiber network (in this case the spider silk) disposed on top of the grid then acts as a matrix forcing a protein which is later added to be placed in a random orientation on the grid, before subsequent single particle reconstruction in (cryo- or negative stain) TEM. Adding a protein directly to the grid 116 often results in that the protein orients itself in a preferred orientation (i.e. laying down when elongated and/or flat), which limits the resolution that can be achieved in the reconstruction.

Experiments

As described above, the microfluidic device of the present invention consists of several layers of different materials, as particularly indicated in, for example, FIG. 3 It was fabricated from hydrophilic sheets (Type C laser printing transparency, Xerox, Elmstock, UK), adhesive tape 1 (64620, Tesa, Norderstedt, Germany) and adhesive tape 2 (300LSE, 3M, VWR, Spånga, Sweden). Low-tack adhesive tape (Scotch® 928, 3M, Amazon, Koblenz, Germany) was used to fixate the 400 mesh TEM grids (01754-F, Ted Pella Inc., Redding, Calif.) which are formvar coated copper grids with a continuous carbon film. Ahlstrom grade 238 and 222 (Ahlstrom Filtration LLC, Mt. Holly Springs, Pa.) were used as absorption paper 1 and absorption paper 2 in the draining or blotting unit, respectively. The soluble film or membrane/valve was fabricated from granular PVA (360627, Sigma-Aldrich, St. Louis, Mo.). AAV (adeno-associated virus) particles, serotype 2 (AAV2) encapsulated with Cytomegalovirus (CMV) promoter-driven expression of Green Fluorescent Protein (GFP), with a stock concentration of $1\times10^{13}$ gc/mL (CV10004-50UL, AMS Biotechnology Ltd., Abingdon, UK) was used as the sample.

The AAV sample was diluted with phosphate-buffered saline (DPBS (−/−) 14190-094, Thermo-Fisher, Uppsala, Sweden) to a concentration of $1\times10^{12}$ gc/mL. 26S proteasome (#: E-350, BostonBiochem, Cambridge, Mass.) was used as a test sample representing a large globular protein complex. The sample with protein fibrils from whey protein isolate (WPI)[16], with an initial concentration of 40 mg/ml, was a gift from the Division of Applied Physical Chemistry at the Royal Institute of Technology in Stockholm, Sweden.

NanoVan®, 2% Methylamine vanadate in solution, (#2011-5ML, Nanoprobes, Yaphank, N.Y.) and Uranyl Acetate 2% in solution (#2240-2, Electron Microscopy Sciences, Hatfield, Pa.) were used as stain. Aqueous solutions of food color dyes (EAN-codes: 5701073064665 and 5701073064672, Dr. Oetker, Coop, Solna, Sweden) were used as models for sample and stain.

Each device was fabricated using lamination technology where the devices were formed by stacking several layers of different materials, as described previously. The cross section in FIG. 3 shows the different layers. The denomination, brand name and thicknesses of these layers were as:

| Denomination | Brand name | Thickness [μm] |
| --- | --- | --- |
| Hydrophilic sheets | Type C laser printing transparency, Xerox | 100 |
| Adhesive tape 1 | 64620, Tesa | 170 |
| Adhesive tape 2 | 300LSE, 3M | 50 |
| Low-tack adhesive | Scotch ® 928, 3M | 30 |
| Paper 1 | Ahlstrom grade 238 | 340 |
| Paper 2 | Ahlstrom grade 222 | 830. |

The adhesives and the hydrophilic sheets were structured using a cutting plotter (CE6000, Graphtec America Inc., Irvine, CA).

The PVA film or membrane was fabricated from an aqueous solution of 20 wt % of granular PVA. Using a thin-film applicator (4340, Elcometer, Manchester, UK) the PVA films were uniformly transferred to laminating pouches (3385694, Office Depot, LA Venlo, Netherlands) and dried at room temperature. The final PVA film thickness was measured using a thickness gauge with 1 μm graduation (2109 L Metric Dial Gauge, Mitutoyo, Upplands Väsby, Sweden).

The PVA film was laminated to absorption paper 2 at 85° C. using a laminator (Heat Seal Pro H600, GBC, Northbrook, Ill.). The paper-PVA laminates were kept in a humidity chamber at 80% relative humidity until 30 minutes before use.

The paper materials, including the paper-PVA laminate, were cut by a laser cutter (VLS 2.30, Universal Laser Systems, Vienna, Austria). After structuring, the layers were assembled by using alignment pins and laminated at room temperature. For improved particle adhesion, the TEM grids were glow discharged in oxygen plasma with a PELCO easiGlow™ (91000S-230, Ted Pella Inc., Redding, Calif.) before fully assembling the microfluidic device of the present invention. A fully assembled fabricated device is shown in FIG. 5. The dimensions of the device are 6×12 mm². The devices were used within one hour after glow discharging the TEM grids.

One important feature of the microfluidic device of the present invention is that it is designed to minimize user-interactions. To demonstrate the autonomous device operation and microfluidic consistency six devices were evaluated. Five devices were used with AAV particles as sample and NanoVan® as stain. The grids from these five devices were used to collect TEM images for an automated image analysis on a total of 225 images. To better visualize the individual preparation steps of the autonomous device, one device was used with color dye solutions. Blue dye solution and yellow dye solution were used as models for sample and stain, respectively. First, 5 μl of stain liquid was added via the stain inlet into the stain reservoir. Then, the autonomous TEM grid preparation mechanism was triggered by adding 5 μl of sample to the sample inlet of the sample reservoir or grid chamber.

The TEM grid preparation sequence of all the devices was recorded with a camera with a frame rate of 50 frames per second. To analyze the device performance and consistency of the autonomous preparation steps, the time interval of each step was manually obtained. The time period between the addition of stain and the addition of the sample liquid (including the particles) was defined as the stain preloading time.

To demonstrate the robustness of the stain reservoir, i.e. stain confinement without leakage, the time between stain and sample addition was varied between 20-60 seconds wherein the stain liquid was held in place by a surface extending between the pinning edge and an underside of a hydrophilic surface i.e. capillary forces and surface tension. As illustrated in FIGS. 1A-1D, the microfluidic TEM grid preparation steps after sample addition includes sample adsorption, draining/blotting and thin film drying. As critical aspect of the method of the present invention is that the adsorption time of the sample on the TEM grid corresponds to and is the same as the dissolving time of the PVA film. It was defined as the time between wetting of paper 1 and the start of the blotting event. The PVA layer thickness was 10 μm. The blotting time is the interval between the start and the end of the draining/blotting event. The start of the blotting event is defined as the moment when the liquid first moves into the draining unit. The end of the blotting event is defined as the moment when the bulk of liquid is drained by the draining unit leaving a thin stain film on the TEM grid. After this, the drying interval starts and lasts until the remaining thin film of stain on the grid was visually dry.

In general, TEM imaging is a powerful visualization technique for many different types of samples. However, the required sample adsorption time varies between different samples. The main reason for this is that sample adsorption depends on the interaction between sample and the carbon surface of the TEM grid. Hence, devices with different adsorption times to account for different sample requirements would be desirable.

Another key element of the microfluidic device of the present invention is the dissolving time of the water-soluble PVA film, that autonomously controls the timing of the device, corresponds to the sample adsorption time of the sample (i.e. film or layer of particles embedded in stain) on the grid.

To demonstrate the adjustability of the adsorption time of the sample on the grid, microfluidic devices with three different thicknesses of the water-soluble film (12 μm, 24 μm and 36 μm) were fabricated and investigated. Among the parameters that affect the dissolving time (e.g. temperature, relative humidity), the thickness of the dissolvable film is one of the easiest parameters to tune and adjust. The PVA thicknesses of 24 μm and 36 μm were achieved by stacking multiple layers of 12 μm PVA sheets and laminating them to paper 2 below the PVA sheets at 85° C. with the laminator. The paper-PVA laminates were kept in a humidity chamber at 80% relative humidity until 30 minutes before use. The adsorption time was evaluated of 15 devices, five devices per film thickness, using 5 μl of blue dye solution and 5 μl of yellow dye solution as a model for sample and stain, respectively.

To assess the sample preparation quality, TEM imaging was performed on the five autonomously prepared TEM grids with AAV particles as sample and NanoVan® as stain. NanoVan® was chosen because it is not radioactive, unlike the commonly used Uranyl Acetate, and can be handled in an ordinary laboratory. For all five grids, it was investigated whether AAVs were successfully adsorbed to the TEM grid and sufficiently embedded in stain. The AAV particles on different magnification levels were inspected, with a field of view (FOV) between 16 μm and 500 nm. The imaging was performed on MiniTEM™ microscopes (Vironova AB, Stockholm, Sweden) with an operating voltage of 25 kV.

To investigate whether the obtained TEM images were useful for automated image analysis, a particle detection script was applied to the TEM images of the five autonomously prepared grids. A total of 225 images were collected according to the imaging scheme shown in FIG. 8. At low magnification, the user manually chose five non-neighboring grid squares. Then, nine high magnification images were acquired per grid square at a FOV of 2 μm, resulting in 45 images per grid. At this magnification, where a pixel represents approximately 1 nm, a number of particles per image can usually be seen and the morphology of the AAVs is typically visible. Grid 1, grid 4 and grid 5 were imaged on the same microscope, while grid 2 and grid 3 were imaged on a second microscope. The particle detection script was applied to all 225 images. AAVs have an icosahedral capsid that appears round and has an expected diameter of 20-25 nm. However, the script was designed to detect the stain envelope around the AAV particles so that the particles appear larger than the actual virus size. Therefore, the particle detection script was set to detect round objects within a diameter range of 24 nm to 32 nm. From the automated image analysis, the number of detected particles per grid were obtained, where each detected particle is characterized by its position and size.

To quantify the particle detection results, a manual particle detection was performed on a subset of 25 of the images, with five randomly chosen images per TEM grid. The number of particles were manually counted and compared with the results from the detection script. This was done to find the ratio of true and false positives, which both are important measures for the performance of the detection script.

nsTEM is routinely used as a quality control during the preparation of biological specimens, e.g. protein complexes, for structural biology. To investigate the potential use of the microfluidic device for wider applications and with different stains, proteasomes were prepared and image, as a larger globular protein complex, and protein fibrils from WPI, as a filamentous protein. The PVA films in the used microfluidic devices had a thickness of 15 μm, corresponding to a dissolving time of around 35 seconds. For the proteasomes and fibrils, stock solution of Uranyl Acetate and NanoVan®, was used, respectively.

As described in detail above, the TEM grid preparation sequence is shown in FIGS. 2A-2D. For visibility, colored dye solutions were used instead of sample and stain solutions. The first step shows how the preloaded stain 208 (yellow dye solution) is contained in the stain reservoir 202 and the sample 210, 214 (blue dye solution) is added (best shown in FIG. 2A. In the second step, the sample 210 including the particles, 214 cover the TEM grid as long as the PVA film or valve is closed (best shown in FIG. 2B. When the PVA film or valve has dissolved, the stain and sample liquids are blotted (best shown in FIG. 2C. Finally, the bulk of liquids is contained in the draining media (blotting filter/paper) and the stain film, including particles embedded therein, dries (best shown in FIG. 2D). Compared to a previously reported microfluidic TEM grid preparation, the user interactions were reduced by providing an autonomous microfluidic operation that is controlled by the water-soluble PVA film. Furthermore, a significantly lower liquid consumption was demonstrated with liquid volumes as small as in the manual preparation protocols.

To demonstrate microfluidic consistency, video recordings were analyzed with respect to timing and duration of the microfluidic events on the five devices used with AAVs as sample and NanoVan® as stain. FIG. 6 presents a bar chart with the time intervals for each of the four sample preparation steps. The results show that regardless of the length of the stain preloading time, all the following steps including adsorption, draining/blotting and drying, are close to identical for the five devices. This demonstrates that the stain reservoir reliably contains the stain until the sample is added irrespective of the stain preloading time. The average adsorption time for the five devices is 10.6±0.3 s, corresponding to a CV of 3%. This indicates a highly consistent autonomous time-control of the microfluidic device of the present invention. The average draining/blotting time is 0.8±0.1 s, corresponding to a CV of 12.5%. While the CV seems high, the absolute deviation is low and confirms the microfluidic consistency of the device of the present invention. The drying step does not end abruptly which makes it difficult to measure the exact drying interval by viewing videos. However, it was observed that all the TEM grids were visually dry within one minute. The reliable and fast drying is enabled by the grid area sized top opening in the grid chamber.

The results show that the microfluidic device of the present invention works as intended although the user input was minimal. Irrespective of the stain preloading time, the autonomous device operation after sample addition is close to identical for the five devices which demonstrates a high microfluidic consistency.

To demonstrate the adjustability of the sample adsorption time, which corresponds to the PVA dissolving time, three different thicknesses (12 μm, 24 μm and 36 μm) of the water-soluble PVA film were tested in the microfluidic device of the present invention. FIG. 7 shows the measurement results of the adsorption time. The dissolving time of the PVA films increases with PVA film thickness. For 12 μm, 24 μm and 36 μm thicknesses of the PVA films, the average dissolving time is 14.4±0.9 s (n=5), 89.9±12.0 s (n=5) and 191.6±20.3 s (n=5), respectively. The results show that it is possible to easily adjust the adsorption time by changing the PVA film thickness. The variation of dissolving time increases with increased PVA film thickness. This could be due to small differences in the PVA film thickness between different devices. However, the variation is low enough to conclude that the adsorption times can be controlled by the design of the PVA layer of the present invention.

TEM imaging of the five autonomously prepared TEM grids made it possible to assess the sample preparation quality. FIGS. 9A-9C show a magnification series with three FOVs: 16 μm, 2 μm and 500 nm. In the largest FOV (16 μm), the AAV particles appear as dark spots. The intermediate FOV (2 μm) shows a higher level of detail. The particles are visible as bright, round objects encircled by dark rings with a radially fading stain gradient. The smallest FOV (500 nm) in this series has the highest level of detail and provides a close-up view of the AAV particles.

FIGS. 10A-10E show one exemplary image from each of the five grids (FOV 2 μm). It was found that all five TEM grids contain well embedded particles in the stain film on the grid, visible as bright spots surrounded by dark stain envelopes. Variations in the appearance of the stain envelope might be due to local variations of stain thickness. Also, thickness variations of the TEM grid, e.g. caused by local inhomogeneities of the carbon film, can result in variations of the image darkness. Overall, the results from the five microfluidic devices showed consistent preparation of TEM grids with well embedded AAV particles.

To further demonstrate sample preparation consistency, 225 TEM images were collected and an automated particle detection was performed. The particle detection script detected 5171 particles in all 225 images. Every grid, with 45 images, contained an average of 1034±65 particles, corresponding to a CV of 6%. This indicates a reproducible and consistent AAV particle spreading over five independently prepared TEM grids. Using the results of the automated particle detection, the detected size of the particles was extracted.

FIG. 11 is a graph 640 that shows the average particle diameter for the detected particles in each grid. Two different microscopes were used and even though the calibrations might be slightly different, the average particle size for each grid is well within the error bars of the other samples. The average size of all detected particles is 28±2 nm (n=5171), corresponding to a CV of 7%. This low variation means that, irrespective of the grid, all detected particles have a similar detected size. The real size of AAV particles is 20-25 nm but appears larger when imaged in nsTEM due to the stain envelope. The detection script is designed to outline and measure particles at the stain layer, i.e. outside the actual particle. Therefore, the detected particle size is well within the expected size window.

The result of the manual particle detection in a subset of 25 images allowed to quantify the automated detection results. FIG. 12 summarizes the results of the subset test. The manual count resulted in 605 particles in the subset. The automated particle script found 557 of these particles correctly (True positives), which corresponds to a success rate of 92%. The script found 29 objects that were not correct (False positives), which corresponds to 4.9%. With true positives above 90% and false positives around 5%, it can be concluded that the images and the autonomous sample preparation have sufficient quality for simple automated image analysis.

Figure 17A:
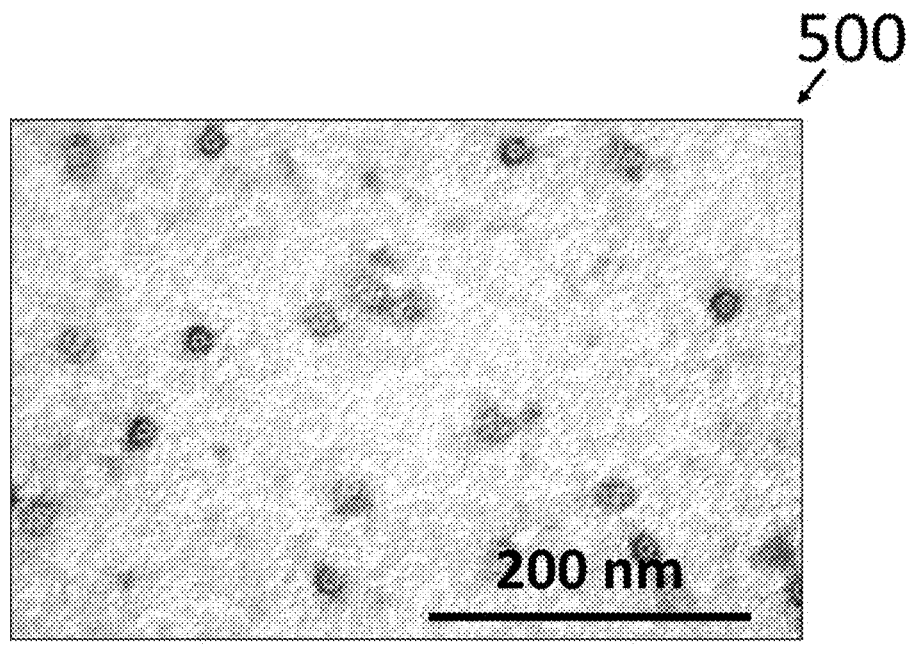
FIG. 17A is an image of proteasomes at a first magnification (the length of 200 nm is shown)
Figure 17B:
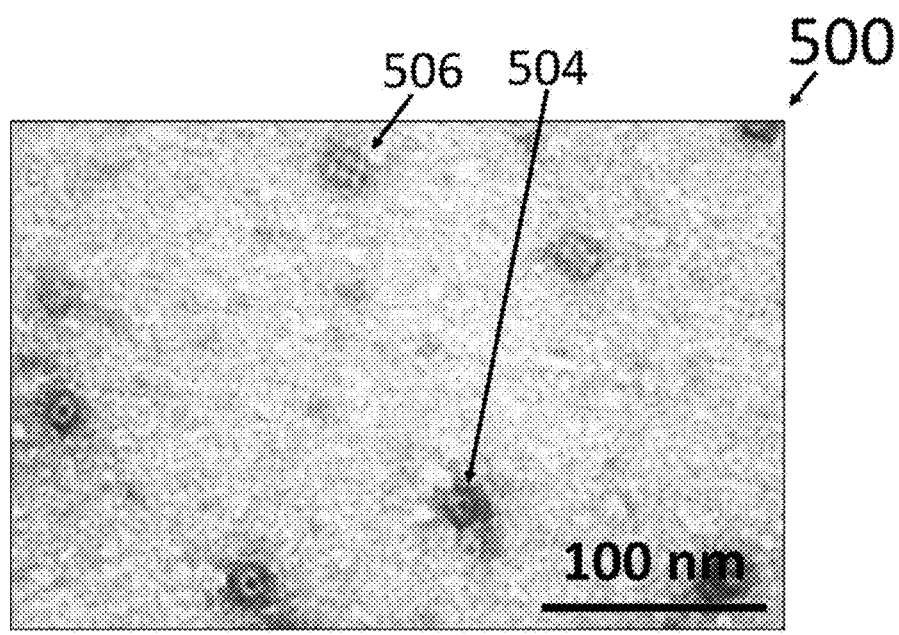
FIG. 17B is an image of proteasomes shown in FIG. 17A at a second magnification (the length of 100 nm is shown)
Figure 17C:
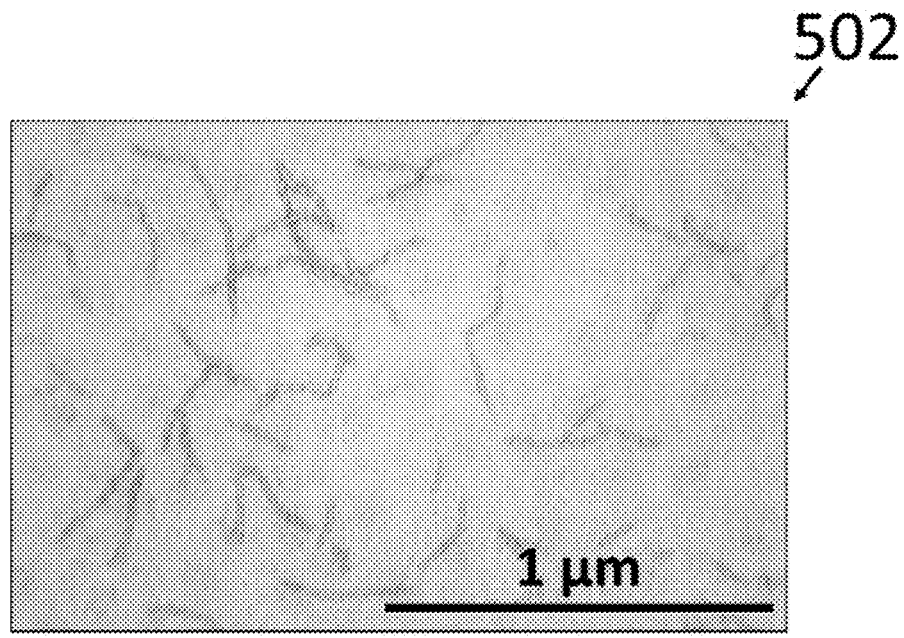
FIG. 17C is an image of protein (WPI) fibrils at a first magnification (the length of 1 µm is shown)
Figure 17D:
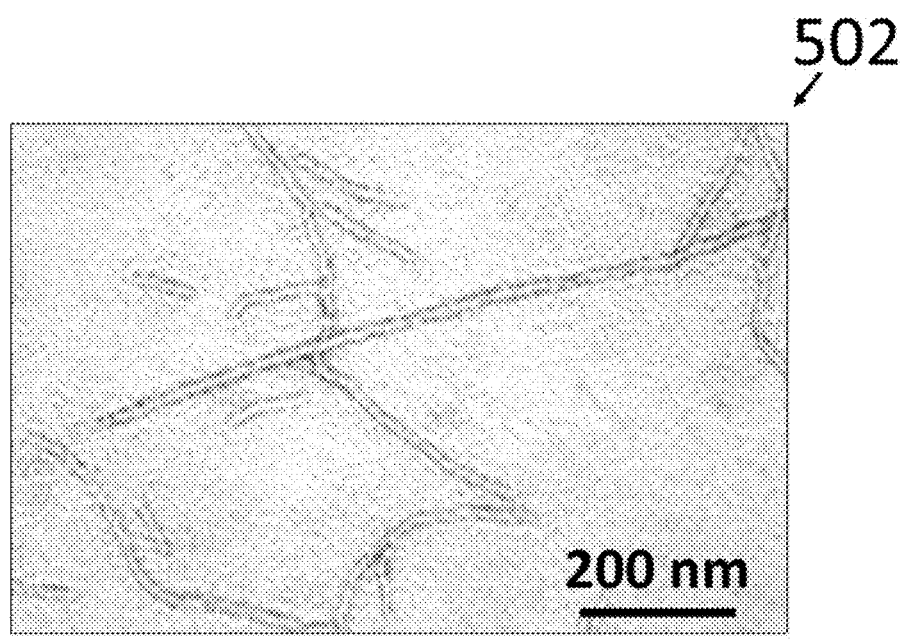
FIG. 17D is an image of the WPI fibrils at a second magnification (the length of 200 nm is shown)

To broaden the scope of applications proteasomes and protein fibrils from WPI were prepared and imaged. The results of those two samples 500, 502, presented in FIGS. 17A-17D, reveal an even spreading of the proteins on the TEM grid with well-embedded areas suitable for TEM investigations. FIGS. 17A-17B show images 500 of 265 proteasomes at two different magnifications. A top view 504 and a side view 506 of the proteasomes can be observed. FIGS. 17C-17D show images of WPI fibrils 508 at two different magnifications. The analysis of the proteasome specimen (best shown in FIGS. 17A-17B) shows that individual proteasomes can clearly be identified, and structural features such as details of the subunits can be distinguished. Different projections can be observed on the images, with the top view appearing as a circular particle and the side view appearing rectangular. The analysis of the WPI fibrils (best shown in FIGS. 17C-17D allows the observation and characterization of well-defined individual fibrils of various lengths. Overall, the morphological observations are in line with reported data of similar samples prepared with conventional manual nsTEM. The preparation of these two protein samples did not require further adjustments of the microfluidic device, hence demonstrating the versatility and robustness of the method.

Below is yet another possible application in the field for the method of the present invention that would require a modified device. The possible nsTEM sample preparation application example is immunogold-labelling where four liquids need to be flushed over the sample. The sequence of preparation steps would be:

1) A grid, with the sample already attached thereto, is added to the device;
2) A primary antibody is permitted to adhere to the grid (so added directly onto the grid as the sample liquid in the description above);
3) Once the binding has occurred, a blocking liquid is flushed over the grid (e.g. BSA=bovine serum albumin, or desiccated milk);
4) Then a second antibody connected to gold particles is flushed over to bind to and hence mark the primary antibody positions; and
5) Finally, non-bound gold particles are washed off with the last washing step.

In summary, a capillary-driven single-use device of the present invention for autonomous TEM sample preparation has been presented. To avoid operator bias and error-prone manual steps, the device of the present invention is designed to minimize user-interactions. The key design elements are the stain and sample reservoirs combined with the water-soluble valve or PVA film and the absorption membranes. These key elements enable the starting of the autonomous TEM grid preparation with only one non-critical user-interaction. The device consistency both for the microfluidic performance and the sample preparation quality have been demonstrated. The consistency of the microfluidic performance was shown by five microfluidic devices with close to identical TEM grid preparation sequences. The sample preparation consistency was demonstrated by five TEM grids that all exhibit well embedded AAV particles. This preparation consistency was further highlighted by the results of the automated particle detection. From a subset test with true positives above 90% and false positives around 5%, it was concluded that the images and the autonomous sample preparation hold sufficient quality for image analysis. The additional preparation of two protein samples demonstrated the versatility of the microfluidic device for a wider scope of applications. Furthermore, the adjustability of timing of the microfluidic events was demonstrated by changing the thickness of the water-soluble valve or PVA film. This allows to account for different sample adsorption requirements. To account for TEM sample preparation requiring different staining times, the device of the present can be extended by a second draining unit. In conclusion, the demonstrated microfluidic device of the present invention presents a promising, effective and reliable solution to alleviate the problems associated with human inconsistency in manual TEM grid preparations.

The evaporation arrangement of the present invention is important and that the sample support is exposed to air for proper evaporation. Another aspect is that the width of the opening and the width of the sample support should be about the same. The humidity condition immediately above the sample support is higher than the humidity outside the opening i.e. above the device. At the liquid boundary of the liquid sample on the sample support the humidity is 100% while the relative humidity in the ambient air outside the device is lower which promotes evaporation of the liquid in the stain layer through the opening. It should be understood that the first liquid can be held in the first reservoir without using an edge. The two liquids can connect without the use of the edge but, for example, putting pressure on one of the liquid droplets. The edge, however, stops the first liquid from flowing into the second reservoir. This is because the edge is a discontinuity in the channel between the two reservoirs and the travel of the capillary force along the wall of the channel is stopped. The first liquid, such as the stain liquid, could be held in the first reservoir i.e. the stain reservoir without using an edge. The pinning edge keeps the stain liquid in place i.e. stops the stain liquid from flowing into the sample reservoir while adding the liquid to the sample reservoir. The expansion (bulging out) of the first liquid between the edge and the hydrophilic upper surface is beneficial but not necessary. It makes the device more robust.

It should also be understood that it is not necessary to use capillary forces to hold the first liquid in the first reservoir. The device preferably, but not necessarily, has a channel going from the first reservoir to the second reservoir. Preferably, the two reservoirs should be in fluid communication and that the first liquid should be held in the first reservoir. This confinement of the first liquid in the first reservoir is preferably but not necessarily based on capillary forces and/or surface tension which are easily broken when the second liquid is added and connects to the first liquid. It is not necessary that the first reservoir is at a higher elevation compared to the second reservoir and the blotting unit. All three units could be located on a common surface at the same elevation.

Preferably, the dissolvable member decides the timing of the adsorption of sample particles on the sample support but this could also be adjusted by using different filters that absorb fluids at different rates. For example, small narrow filter slows down the absorption rate. The drainage in micro channels could also acts as a delay mechanism and drainage speed control. It may also be necessary to have a minimum speed or a certain delay time to give enough time for the sample particles to adhere to the sample support or grid. It may also be necessary to have a high speed when draining the first liquid (stain) in order to leave a stain layer. If the draining of the first liquid is too slow, too much stain will be drained leaving the particles unprotected. This results in a poor-quality preparation. It should be noted that although the dissolvable membrane or film delays the liquid flow and once the membrane is dissolved the flow rate is quite rapid as opposed to a very slow constant flow rate.

While the present invention has been described in accordance with preferred compositions and embodiments, it is to be understood that certain substitutions and alterations may be made thereto without departing from the spirit and scope of the following claims.

We claim:

1. A method of preparing a sample in a microfluidic device, comprising:
   providing a microfluidic device having a first reservoir in fluid communication with a second reservoir in fluid communication with and adjacent to a draining unit having a first absorbing member disposed therein, the first reservoir containing a first liquid, the first liquid being held in the first reservoir by a capillary stop valve connecting the first and second reservoirs, the second reservoir having a sample support disposed therein;
   adding a second liquid, containing substances, to the second reservoir;
   the second liquid contacting the first liquid and the first absorbing member;
   the first absorbing member absorbing the second liquid and the first liquid; and
   the substances adhering to the sample support.

2. The method of claim 1 wherein the method further comprises the steps of providing the draining unit with a dissolvable membrane upstream of the first absorbing member, the second liquid dissolving the dissolvable membrane prior to the first absorbing member absorbing the first and second liquids.

3. The method of claim 1 wherein the method further comprises the steps of the substances adhering to the sample support while the second liquid dissolving a dissolvable membrane.

4. The method of claim 1 wherein the method further comprises the step of the capillary stop valve holding the first liquid in the first reservoir preventing the first liquid from flowing into the second reservoir prior to adding the second liquid to the second reservoir.

5. The method of claim 1 wherein the method further comprises the step of a portion of the first liquid embedding the substances adhered to the sample support.

6. The method of claim 1 wherein the method further comprises the steps of providing the capillary stop valve with an edge that separates the first reservoir from the second reservoir, the edge holding the first liquid in the first reservoir.

7. The method of claim 2 wherein the method further comprises the steps of providing the dissolvable membrane downstream of the first absorption member and a second absorption member downstream of the dissolvable membrane, the first absorption member absorbing the second liquid and permitting the second liquid to come into contact with the dissolvable member.

8. The method of claim 7 wherein the method further comprises the step of the second absorption member absorbing the second liquid and the first liquid after the dissolvable membrane has been dissolved.

9. The method of claim 1 wherein the method further comprises the step of the second liquid breaking a surface tension of the first liquid upon contact with the first liquid held in the capillary stop valve.

10. The method of claim 1 wherein the method further comprises the step of a time period required to dissolve the dissolvable membrane controlling a permitted time period for the substances to adhere to the sample support.

11. The method of claim 1 wherein the method further comprises the step of the second liquid contacting the absorbing member before the first liquid.

12. The method of claim 5 wherein the method further comprises the step of the first portion of the first liquid drying on the sample support.

13. The method of claim 1 wherein the method further comprises a portion of the first liquid forming a liquid film on the sample support, wherein the liquid film has a film thickness of less than 1 mm.

14. The method of claim 1 wherein the sample support is dried within three minutes at an ambient temperature and 50% relative humidity.

15. The method of claim 1, wherein the first liquid has a volume of between 0.1-50 µl.

16. The method of claim 1 wherein the second liquid has a volume of between 0.1-50 µl.

17. A method of preparing a sample in a microfluidic device, comprising:
   providing a microfluidic device having a first reservoir in fluid communication with a second reservoir in fluid communication with and adjacent to a draining unit having a first absorbing member disposed therein, the first reservoir containing a first liquid, the first liquid being held in the first reservoir by a capillary stop valve connecting the first and second reservoirs;

a user of the microfluidic device adding a sample support into the second reservoir;

the user adding a second liquid, containing substances, to the second reservoir;

the user waiting a waiting period of at least 20 seconds before removing the sample support from the second reservoir;

during the waiting period, the second liquid contacting the first liquid and the first absorbing member;

during the waiting period, the first absorbing member absorbing the second liquid and the first liquid;

during the waiting period, the substances adhering to the sample support; and at the end of the waiting period, the user removing the sample support from the second reservoir.

18. The method of claim 17 wherein the method further comprises the steps of providing the draining unit with a dissolvable membrane upstream of the first absorbing member and the second liquid dissolving the dissolvable member during the waiting period.

19. The method of claim 17 wherein the method further comprises the steps of the first liquid forming a film on the sample support and embedding substances adhered to sample support.

20. The method of claim 19 wherein the method further comprises the step of the film drying on the sample support.

* * * * *